United States Patent
Yi

(10) Patent No.: US 10,337,995 B2
(45) Date of Patent: Jul. 2, 2019

(54) SYSTEMS AND METHODS FOR OBLIQUE LASER SCANNING

(71) Applicant: BOSTON MEDICAL CENTER CORPORATION, Boston, MA (US)

(72) Inventor: Ji Yi, Brookline, MA (US)

(73) Assignee: BOSTON MEDICAL CENTER CORPORATION, Boston, MA (US)

(*) Notice: Subject to any disclaimer, the term of this patent is extended or adjusted under 35 U.S.C. 154(b) by 0 days.

(21) Appl. No.: 16/005,246

(22) Filed: Jun. 11, 2018

(65) Prior Publication Data

US 2018/0356344 A1 Dec. 13, 2018

Related U.S. Application Data

(60) Provisional application No. 62/518,248, filed on Jun. 12, 2017.

(51) Int. Cl.
*G01N 21/64* (2006.01)
*G01J 3/02* (2006.01)
(Continued)

(52) U.S. Cl.
CPC ....... *G01N 21/6458* (2013.01); *A61B 5/0066* (2013.01); *A61B 5/0071* (2013.01);
(Continued)

(58) Field of Classification Search
CPC .............. G01N 21/6458; G01N 21/47; G01N 21/6402; G01N 2021/1787; G01J 3/0208; G01J 3/4406; G02B 26/085; G02B 26/105
(Continued)

(56) References Cited

U.S. PATENT DOCUMENTS

2002/0171831 A1   11/2002  Backman et al.
2008/0186477 A1*  8/2008  Wang .................. G01N 21/253
                                              356/73
(Continued)

OTHER PUBLICATIONS

Baran, U. et al., "Review of optical coherence tomography based angiography in neuroscience," Neurophotonics 3(1), 010902, Jan.-Mar. 2016 (13 pages).

(Continued)

*Primary Examiner* — Hina F Ayub
(74) *Attorney, Agent, or Firm* — Nixon Peabody LLP; Ronald I. Eisenstein; David F. Crosby

(57) ABSTRACT

A method for constructing a three-dimensional image of a sample includes producing electromagnetic radiation and directing the produced electromagnetic radiation such that it is incident on the sample at an oblique angle. The incident electromagnetic radiation is scanned in discrete increments to a plurality of discrete locations along a first direction, and at each discrete location, scanned along a second direction orthogonal to the first direction. The sample reflects a first portion of the incident electromagnetic radiation and absorbs a second portion of the incident electromagnetic radiation, and emits electromagnetic radiation responsive to the absorption. A plurality of cross-sectional images is produced from the reflected electromagnetic radiation and the emitted electromagnetic radiation, and each cross-sectional image is modified to compensate for the oblique angle. The modified cross-sectional images are then combined to create a three-dimensional image of the sample.

20 Claims, 17 Drawing Sheets

(51) Int. Cl.
G01J 3/44 (2006.01)
G02B 26/08 (2006.01)
G01N 21/47 (2006.01)
G02B 26/10 (2006.01)
A61B 5/00 (2006.01)
G01B 9/02 (2006.01)
G01N 21/17 (2006.01)

(52) U.S. Cl.
CPC ........ *G01B 9/02091* (2013.01); *G01J 3/0208* (2013.01); *G01J 3/4406* (2013.01); *G01N 21/47* (2013.01); *G01N 21/4795* (2013.01); *G01N 21/6402* (2013.01); *G02B 26/085* (2013.01); *G02B 26/105* (2013.01); *G01N 2021/1785* (2013.01); *G01N 2021/1787* (2013.01)

(58) Field of Classification Search
USPC .......................................................... 356/73
See application file for complete search history.

(56) References Cited

U.S. PATENT DOCUMENTS

| | | |
|---|---|---|
| 2013/0095519 A1 | 4/2013 | Backman et al. |
| 2014/0321772 A1* | 10/2014 | Piche ................... G02B 21/002 382/284 |
| 2015/0348287 A1 | 12/2015 | Yi et al. |
| 2016/0213252 A1 | 7/2016 | Hillman et al. |
| 2016/0327779 A1 | 11/2016 | Hillman |
| 2017/0150887 A1 | 6/2017 | Zuckerman |
| 2018/0306720 A1* | 10/2018 | Wang ................. G01N 21/6458 |

OTHER PUBLICATIONS

Barer, R. et al., "Refractive index of concentrated protein solutions," Nature, No. 4409, May 1, 1954, pp. 821-822 (2 pages).
Bouchard, M.B. et al., "Swept confocally-aligned planar excitation (SCAPE) microscopy for high-speed volumetric imaging of behaving organisms," Nat Photonics. 9(2), Feb. 2015, pp. 113-119 (16 pages).
Chen, C.-L. et al., "Optical coherence tomography based angiography [Invited]," Biomedical Optics Express, vol. 8, No. 2, Feb. 1, 2017, pp. 1056-1082 (27 pages).
Cheng, J.-X., "Coherent Anti-Stokes Raman Scattering Microscopy," Applied Spectroscopy, vol. 61, No. 9, 2007, pp. 197A-208A (12 pages).
Cherkezyan, L. et al., "Interferometric Spectroscopy of Scattered Light Can Quantify the Statistics of Subdiffractional Refractive-Index Fluctuations," Physical Review Letters PRL 111, 033903, 2013 (5 pages).
Claxton, N.S. et al., "Laser scanning confocal microscopy," Department of Optical Microscopy and Digital Imaging, Florida State University, Tallahassee, 2006 (37 pages).
Dai, C. et al., "Simultaneous optical coherence tomography and autofluorescence microscopy with a single light source," Journal of Biomedical Optics, vol. 17(8), 0805021, Aug. 2012 (4 pages).
Davies, H.G. et al., "The Use of the Interference Microscope to Determine Dry Mass in Living Cells and as a Quantitative Cytochemical Method," Quarterly Journal of Microscopical Science vol. 9, part 3, Sep. 1954, pp. 271-304 (38 pages).
Denk, W. et al., "Two-photon laser scanning fluorescence microscopy," Science, vol. 248, No. 4951, Apr. 6, 1990, pp. 73-76 (6 pages).
Dunsby, C., "Optically sectioned imaging by oblique plane microscopy," Optics Express, vol. 16, No. 25, 20306, Dec. 8, 2008 (11 pages).
Evans, C.L. et al., "Chemical imaging of tissue in vivo with video-rate coherent anti-Stokes Raman scattering microscopy," Proceedings of the National Academy of Sciences of the United States of America, vol. 102, No. 46, Nov. 15, 2005, pp. 16807-16812 (6 pages).
Fatehullah, A. et al., "Organoids as an in vitro model of human development and.disease," Nature Cell Biology, vol. 18, No. 3, Mar. 2016, pp. 246-254 (9 pages).
Freudiger, C.W. et al., "Label-Free Biomedical Imaging with High Sensitivity by Stimulated Raman Scattering Microscopy," Science, vol. 322, Dec. 19, 2008, pp. 1857-1861 (5 pages).
Georgakoudi, I. et al., "Optical imaging using endogenous contrast to assess metabolic state," Annual Review of Biomedical Engineering, 14, 2012, pp. 351-367 (19 pages).
Hell, S.W. et al., "Breaking the diffraction resolution limit by stimulated emission: stimulated-emission-depletion fluorescence microscopy," Optics Letters, vol. 19, No. 11, Jun. 1, 1994, pp. 780-782 (3 pages).
Izatt, J.A. et al., "In vivo bidirectional color Doppler flow imaging of picoliter blood volumes using optical coherence tomography," Optics Letters, vol. 22, No. 18, Sep. 15, 1997, pp. 1439-1441 (3 pages).
Keller, P.J. et al., "Reconstruction of Zebrafish Early Embryonic Development by Scanned Light Sheet Microscopy," Science, vol. 322, Nov. 14, 2008, pp. 1065-1069 (6 pages).
Leitgeb, R.A. et al., "Real-time measurement of in vitro flow by Fourier-domain color Doppler optical coherence tomography," Optics Letters, vol. 29, No. 2, Jan. 15, 2004, pp. 171-173 (3 pages).
Radosevich, A.J. et al., "Structural length-scale sensitivities of reflectance measurements in continuous random media under the Born approximation," Optics Letters, vol. 37, No. 24, Dec. 15, 2012, pp. 5220-5222 (3 pages).
Skala, M.C. et al., "In vivo multiphoton microscopy of NADH and FAD redox states, fluorescence lifetimes, and cellular morphology in precancerous epithelia," Proceedings of the National Academy of Sciences, vol. 104, No. 49, Dec. 4, 2007, pp. 19494-19499 (6 pages).
Song, W. et al., "Integrating photoacoustic ophthalmoscopy with scanning laser ophthalmoscopy, optical coherence tomography, and fluorescein angiography for a multimodal retinal imaging platform," Journal of Biomedical Optics 17(6), 0612061, Jun. 2012 (8 pages).
Spence, J.R. et al., "Directed differentiation of human pluripotent stem cells into intestinal tissue in vitro," Nature, vol. 470, Feb. 3, 2011, pp. 105-109 (6 pages).
Tang, S. et al., "Multimodal optical imaging with multiphoton microscopy and optical coherence tomography," Journal of Biophotonics 5, 2012, pp. 396-403 (8 pages).
Urban, B.E. et al., "Super-resolution two-photon microscopy via scanning patterned illumination," Physical Review, E 91, 042703, 2015 (6 pages).
Yaseen, M.A. et al., "Multimodal optical imaging system for in vivo investigation of cerebral oxygen delivery and energy metabolism," Biomedical Optics Express, vol. 6, No. 12, Dec. 1, 2015, pp. 4994-5007 (14 pages).
Yi, J. et al., "Can OCT be sensitive to nanoscale structural alterations in biological tissue?," Optics Express, vol. 21, No. 7, Apr. 8, 2013, pp. 9043-9059 (17 pages).
Yi, J. et al., "Visible-light optical coherence tomography for retinal oximetry," Optics Letters, 38(11), Jun. 1, 2013, pp. 1796-1798 (9 pages).
Yi, J. et al., "Visible light optical coherence tomography measures retinal oxygen metabolic response to systemic oxygenation," Light: Science & Applications, 4, e334, 2015 (10 pages).
Zipfel, W.R. et al., "Live tissue intrinsic emission microscopy using multiphoton-excited native fluorescence and second harmonic generation," Proceedings of the National Academy of Sciences, vol. 100, No. 12, Jun. 10, 2003 pp. 7075-7080 (6 pages).
Booysen, DJ, "A review of fundus autofluorescence imaging," The South African Optometrist, 2013, vol. 72, No. 1, pp. 46-53 (8 pages).
Fleckenstein, M. et al., "Fundus Autofluorescence Imaging in Clinical Use," Review of Ophthalmology, Aug. 12, 2010 (19 pages).
Shahid, K., "Fundamentals of Fundus Autofluorescence Imaging," Review of Optometry, Jan. 2013 (19 pages).

(56) References Cited

OTHER PUBLICATIONS

Pahlevaninezhad, H. et al., "Optical Coherence Tomography and Autofluorescence Imaging of Human Tonsil," PloS ONE, Dec. 26, 2015, vol. 9, No. 12 (11 pages).
Yi, J. et al., "Spatially resolved optical and ultrastructural properties of colorectal and pancreatic field carcinogenesis observed by inverse spectroscopic optical coherence tomography," Journal of Biomedical Optics, Mar. 2014, vol. 19, No. 3 (17 pages).
International Search Report and Written Opinion of International Searching Authority for International Application No. PCT/US18/36948, dated Aug. 30, 2018 (11 pages).

\* cited by examiner

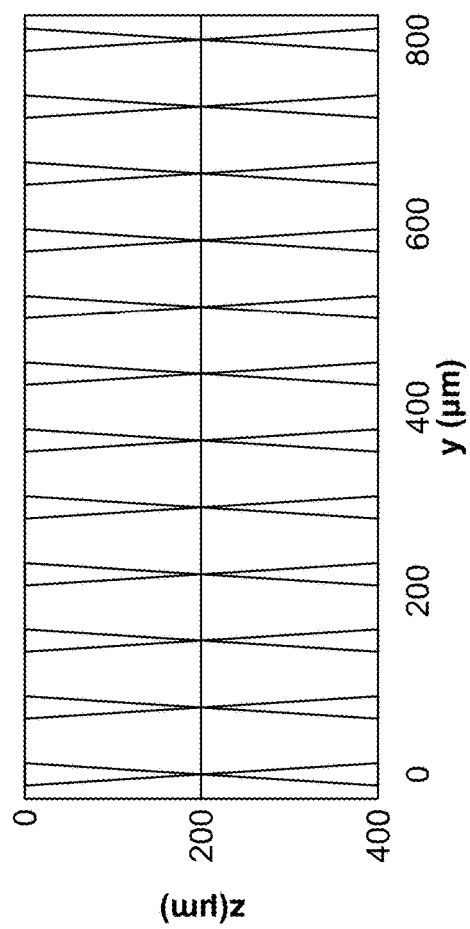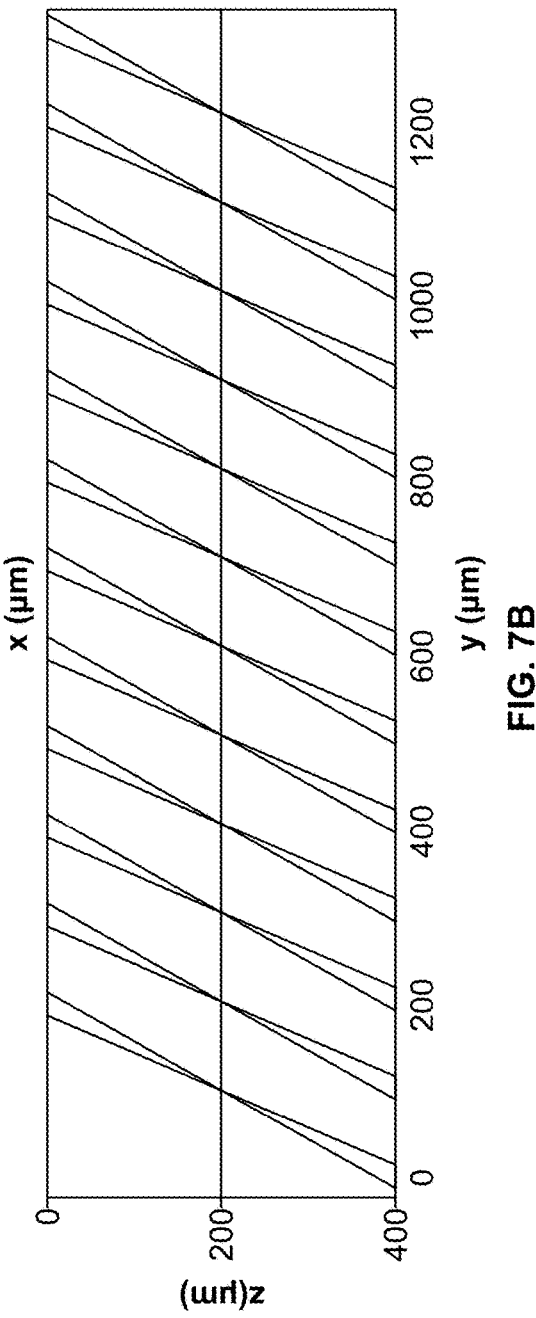

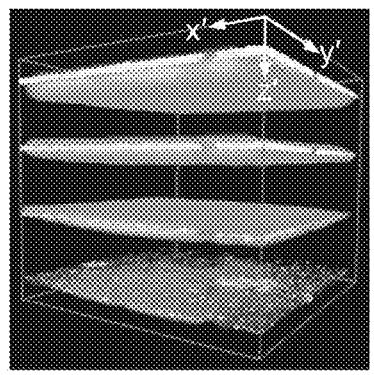
FIG. 13
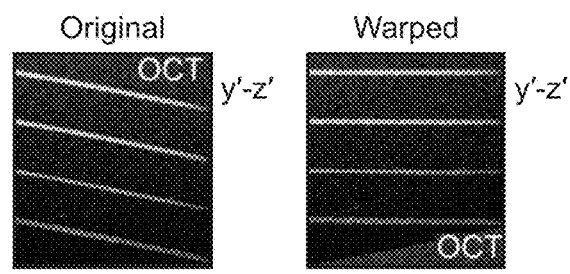
FIG. 14A  FIG. 14B
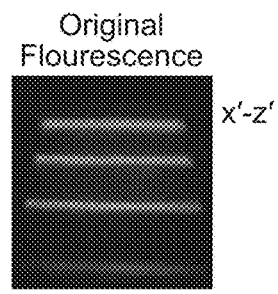
FIG. 15A
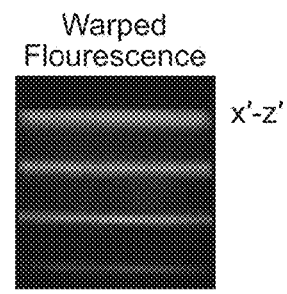
FIG. 15B
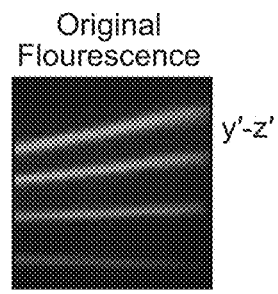
FIG. 16A
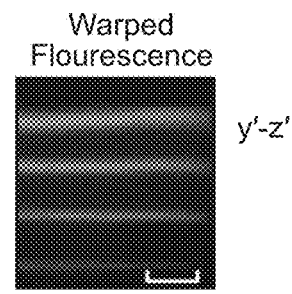
FIG. 16B

OCT

Fluorescence

Overlay

SYSTEMS AND METHODS FOR OBLIQUE LASER SCANNING

CROSS-REFERENCE TO RELATED APPLICATIONS

This application claims the benefit of and priority to U.S. Provisional Patent Application Ser. No. 62/518,248, filed on Jun. 12, 2017, entitled "Systems and Methods for Oblique Laser Scanning," which is hereby incorporated by reference herein in its entirety.

STATEMENT REGARDING FEDERALLY SPONSORED RESEARCH

This invention was made with Government Support under Contract No. CA183101 awarded by the National Institutes of Health. The Government has certain rights in the invention.

TECHNICAL FIELD

The present disclosure relates to optical imaging systems. Specifically, the present disclosure relates to combining separate schema for obtaining structural images and for obtaining fluorescence microscopy images.

BACKGROUND

Optical coherence tomography is an optical imaging technique that allows for resolution of structural aspects of a sample. However, this technique can present limitations on depth penetration and depth resolution, as well as imaging speed. For example, to obtain a high depth resolution, an objective lens with a high numerical aperture is often required, which can limit the field of view. Fluorescence microscopy is an optical imaging technique that allows for the resolution of molecular aspects of the sample, and can supplement some of the limitations of optical coherence tomography. However, each technique generally has different mechanisms for depth discrimination, which are generally not compatible with each other. Constructing three-dimensional images of samples using both optical coherence tomography techniques and fluorescence microscopy techniques can be difficult and time consuming, due to the repeated scans of the sample that are needed.

Aspects of the present disclosure provide a new optical imaging system and methods that solves this problem and other problems.

SUMMARY

According to aspects of the present disclosure, an optical system for producing a three-dimensional image of a sample comprises one or more electromagnetic radiation sources configured to produce electromagnetic radiation; a first optical pathway disposed between the one or more electromagnetic radiation sources and the sample, the produced electromagnetic radiation propagating in a first direction along an optical axis of the first optical pathway towards the sample; a lens disposed in the first optical pathway adjacent to the sample to focus the produced electromagnetic radiation onto the sample, an optical axis of the lens being offset from the optical axis of the first optical pathway such that the produced electromagnetic radiation is incident on the sample at an oblique angle, the sample reflecting a first portion of the incident electromagnetic radiation to produce reflected electromagnetic radiation, the sample absorbing a second portion of the incident electromagnetic radiation and responsive to the absorption of the second portion of the incident electromagnetic radiation, the sample emitting electromagnetic radiation; a second optical pathway disposed between the sample and a first image capture device, the reflected electromagnetic radiation propagating along the second optical pathway from the sample to the first image capture device, the reflected electromagnetic radiation being indicative of structural properties of the sample; and a third optical pathway disposed between the sample and a second image capture device, the emitted electromagnetic radiation propagating along the third optical pathway from the sample to the second image capture device, the emitted electromagnetic radiation being indicative of molecular properties of the sample.

According to aspects of the present disclosure, a method for producing a three-dimensional image of a sample comprises producing electromagnetic radiation from an electromagnetic radiation source; directing the produced electromagnetic radiation such that the produced electromagnetic radiation is incident on the sample at an oblique angle, the sample reflecting a first portion of the incident electromagnetic radiation to produce reflected electromagnetic radiation, the sample absorbing a second portion of the incident electromagnetic radiation and responsive to the absorption, emitting electromagnetic radiation; scanning the incident electromagnetic radiation across the surface of the sample in a first direction, the incident electromagnetic radiation being scanned in discrete increments to a plurality of discrete locations on the surface of the sample; for each discrete location on the surface of the sample, scanning the incident electromagnetic radiation across the surface of the sample in a second direction orthogonal to the first direction; recording the reflected electromagnetic radiation while scanning the incident electromagnetic radiation across the surface of the sample to produce a first plurality of cross-sectional images of the sample; recording the emitted electromagnetic radiation while scanning the incident electromagnetic radiation across the surface of the sample to produce a second plurality of cross-sectional images of the sample; modifying the first and second plurality of cross-sectional images to compensate for the oblique angle of the incident electromagnetic radiation; combining each of the first plurality of modified cross-sectional images to create a first three-dimensional image of the sample; combining each of the second plurality of modified cross-sectional images to create a second three-dimensional image of the sample; and co-registering the first three-dimensional image of the sample and the second three-dimensional image of the sample to create a third three-dimensional image of the sample.

According to aspects of the present disclosure, a method of obtaining a three-dimensional image of a sample comprises producing electromagnetic radiation from one or more electromagnetic radiation sources; directing the produced electromagnetic radiation such that the produced electromagnetic radiation propagates through a lens and is incident on the sample at an oblique angle, the sample reflecting a first portion of the incident electromagnetic radiation to produce reflected electromagnetic radiation, the sample absorbing a second portion of the incident electromagnetic radiation and responsive to the absorption of the second portion of the incident electromagnetic radiation, the sample emitting electromagnetic radiation; scanning the incident electromagnetic radiation across a surface area of the sample; recording the reflected electromagnetic radiation while scanning the incident electromagnetic radiation across the surface of the sample to produce a first plurality of cross-sectional images of the sample; recording the emitted electromagnetic radiation while scanning the incident electromagnetic radiation across the surface of the sample to produce a second plurality of cross-sectional images of the sample; modifying the first and second plurality of cross-sectional images to compensate for the oblique angle of the incident electromagnetic radiation; and producing a three-dimensional image from the first plurality of modified cross-sectional images and the second plurality of modified cross-sectional images.

According to aspects of the present disclosure, an optical system for producing a three-dimensional image of a sample comprises a first electromagnetic radiation source configured to produce electromagnetic radiation in a first wavelength range; a second electromagnetic radiation source configured to produce electromagnetic radiation in a second wavelength range; one or more optical combination components configured to combine the electromagnetic radiation in the first wavelength range and the electromagnetic radiation in the second wavelength range, the combined electromagnetic radiation including a first portion of electromagnetic radiation in the first wavelength range and a second portion of electromagnetic radiation in the second wavelength range; a first optical pathway disposed between the one or more optical combination components and the sample, the combined electromagnetic radiation from the one or more optical combination components configured to propagate along the first optical pathway in a first direction such that it is incident on the sample, the sample reflecting the first portion of the combined electromagnetic radiation to produce reflected electromagnetic radiation, the sample absorbing the second portion of the combined electromagnetic radiation and responsive to the absorption of the second portion of the combined electromagnetic radiation, the sample emitting electromagnetic radiation, the reflected electromagnetic radiation and the emitted electromagnetic radiation propagating along the first optical pathway in a second direction; and an optical separation component disposed in the first optical pathway, the optical separation component directing the reflected electromagnetic radiation along a second optical pathway to a first image capture device and directing the emitted electromagnetic radiation along a third optical pathway to a second image capture device, the reflected electromagnetic radiation being indicative of structural properties of the sample, the emitted electromagnetic radiation being indicative of molecular properties of the sample.

These and other capabilities of the invention, along with the invention itself, will be more fully understood after a review of the following figures, detailed description, and claims.

BRIEF DESCRIPTION OF THE DRAWINGS

The disclosure will be better understood from the following description of exemplary embodiments together with reference to the accompanying drawings.

FIG. 7A shows the x-z longitudinal cross section of a sample being illuminated by electromagnetic radiation, according to aspects of the present disclosure;

FIG. 7B shows the y-z longitudinal cross section of a sample being illuminated by electromagnetic radiation, according to aspects of the present disclosure;

FIG. 13 shows a three-dimensional image of a four-layer fluorescein solution, according to aspects of the present disclosure;

FIG. 14A shows a y-z cross section of the four-layer fluorescein solution of FIG. 13 captured using optical coherence tomography techniques, according to aspects of the present disclosure;

FIG. 14B shows a modified version of the y-z cross section of FIG. 14A;

FIG. 15A shows an x-z cross section of the four-layer fluorescein solution of FIG. 13 captured using fluorescence microscopy techniques, according to aspects of the present disclosure;

FIG. 15B shows a modified version of the x-z cross section of FIG. 15A;

FIG. 16A shows a y-z cross section of the four-layer fluorescein solution of FIG. 13 captured using fluorescence microscopy techniques, according to aspects of the present disclosure;

FIG. 16B shows a modified version of the y-z cross section of FIG. 16A;

Figure 1:
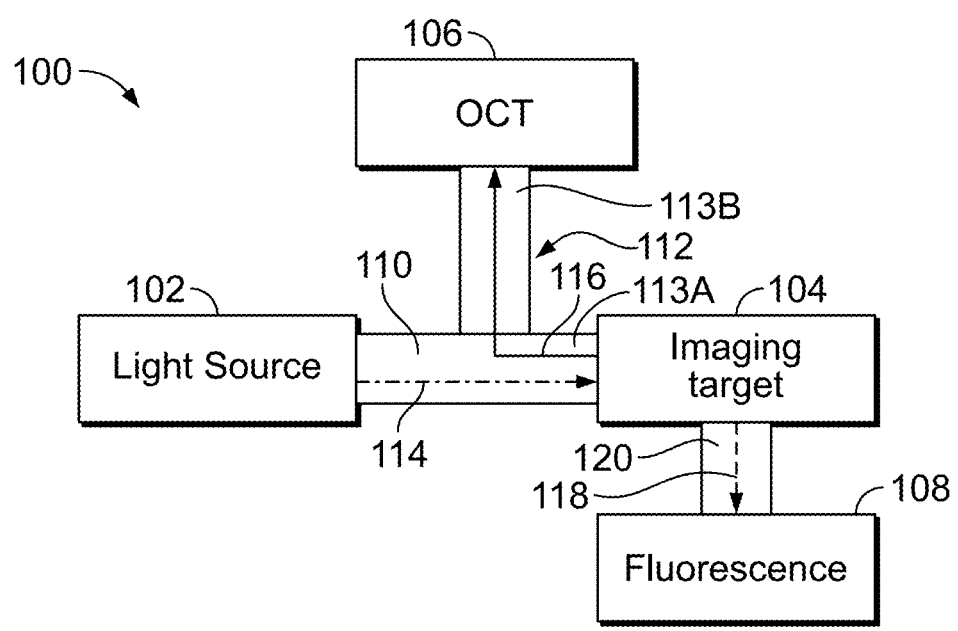
FIG. 1 shows an embodiment of a system for obtaining a three-dimensional image of a sample, according to aspects of the present disclosure.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation." Additionally, the singular terms "a," "an," and "the" include plural referents unless context clearly indicates otherwise.

The system of the present invention utilizes both optical coherence tomography (OCT) techniques and laser scanning fluorescence microscopy (FM) techniques to obtain three-dimensional images of samples or objects within sample. OCT involves measuring electromagnetic radiation reflected off of a sample to obtain a 3D image of the sample. Generally, an OCT system is divided into a reference path and a target path. The target path has the sample to be imaged disposed at one end thereof. The reference path generally has a mirror disposed at the end thereof. In an exemplary setup, electromagnetic radiation is produced and is directed to a half-silvered mirror or other component that splits the electromagnetic radiation into two light rays traveling at 90° relative to each other. One light ray propagates down the reference path, strikes the mirror, and propagates back to the half-silvered mirror. The other light ray propagates down the sample path, strikes the sample, and propagates back to the half-silvered mirror. There, the two light rays combine and propagate to a detector where they form an interference profile that is indicative of the different path lengths traveled by the electromagnetic radiation down the reference path and the sample path. As the distance between the half-silvered mirror and the movable mirror at the end of the reference path is known, this interference profile can be used to determine information about the distance traveled by the light ray reflected off of the sample, and thus the structure of the sample itself. In accordance with some embodiments of the invention, the electromagnetic radiation traveling along the sample path toward the target can be configured to be incident on the target at a predefined oblique angle.

Some of the electromagnetic radiation that strikes the sample will be reflected by the outer surface of the sample, while some of the electromagnetic radiation will penetrate into the interior of the sample and can reflect off of structures located at a depth within the sample. Generally, the electromagnetic radiation propagating in the sample path toward the sample has a narrow spread such that the electromagnetic radiation is effectively concentrated at a single point on the surface of the sample. This electromagnetic radiation can thus give information about structures located within the sample that are generally in line with point on the surface of the sample.

Interference profiles obtained from a beam of electromagnetic radiation concentrated at one point on the surface of the sample thus gives a "depth profile" at that point. These depth profiles are commonly called "A-scans" or "A-line." Cross-sectional images of the sample, or "B-scans," can be obtained by scanning the beam of electromagnetic radiation across the surface of the sample in a first lateral direction. By then scanning the beam of electromagnetic radiation across the surface of the sample in a second lateral direction orthogonal to the first lateral direction, a plurality of cross-sectional images are obtained that can be obtained to form a 3D image of the sample, which shows structural details about portions of the sample below the surface. OCT is thus able to provide 3D images of the sample with a single scan across the 2D surface of the sample without having to repeat the scan at a multiple different depth levels.

OCT is generally capable of micron and sub-micron resolution, and can generally penetrate into a sample a depth of up to approximately several millimeters. Because OCT relies on elastic light scattering, i.e. light scattering off of the sample due to physical characteristics, molecular composition of the sample does not affect the image. OCT is thus very sensitive to structural changes, even at sub-diffractional length scales (e.g. several tens of nanometers). OCT systems can also be used to measure blood flow, oxygenation, and capillary-level angiography, which make it a useful technique for viewing and characterizing biological tissue.

Fluorescence microscopy is a separate optical imaging technique that enables the capture of images detailing the specific molecular composition of structures within a sample. Generally, the sample or the structures within are treated with selected fluorescent dyes or antibodies, generally known as fluorophores. Fluorophores are chemical compounds that are able to absorb a specific wavelength range of electromagnetic radiation, and in response, emit a specific wavelength range of electromagnetic radiation. The use of other mechanisms to detect fluorescence is also possible, such as intrinsically expressed green fluorescent protein (GFP) fluorescence, autofluorescence from Flavin proteins, and exogenous antibody-conjugated dyes. The fluorophores can also be naturally occurring in the sample.

In a fluorescence microscopy system, the fluorophores and the incident electromagnetic radiation are selected such that the sample (more specifically, the fluorophores in and on the sample) absorb at least a portion of the incident electromagnetic radiation. Electromagnetic radiation is then emitted in response, which can be measured by a camera or other similar device. Fluorescence microscopy systems generally have a scalable resolution a range of sub-microns to microns, and a penetration depth into cells and tissues of microns to millimeters.

Systems and methods according to the present disclosure combine both OCT and fluorescence microscopy to produce a 3D image of the sample and the structures within that provides detail about both structural properties of the sample and molecular properties of the sample. By scanning the sample with the laser at an oblique angle, i.e. by scanning incident electromagnetic radiation across the surface of the sample at an oblique angle, the system can simultaneously obtain 3D OCT images showing structural details, and 3D FM images showing molecular details. These images can be combined into a single 3D image to give a complete structural and molecular picture of the sample. Exemplary samples that can be images by the systems and methods disclosed herein include human and animal retinas, human intestinal organoids (HIOs), and colon mucosa.

As used herein, "2D" means "two-dimensional" and "3D" means "three-dimensional."

As used herein, "electromagnetic radiation" refers to the output of a light source (e.g., including light in the visible and invisible spectrum), and may include electromagnetic waves or their quanta, photons, propagating at a variety of different predefined wavelengths and frequencies.

Referring now to FIG. 1, an embodiment of a system 100 for capturing a 3D image of an imaging target generally includes a light source 102, an imaging target 104, a first image capture device 106 configured to capture a 3D image of the imaging target 104 via optical coherence tomography (OCT) techniques, and a second image capture device 108 configured to capture a 3D image of the imaging target via fluorescence microscopy (FM) techniques. In an embodiment, the first image capture device 106 is a line scan camera. In a further embodiment, the second image capture device 108 is a photomultiplier tube (PMT) array. A PMT array is generally appropriate if a large dynamic range is needed, or if the signal to be recorded will be rapidly changing. In another embodiment, the second image capture device 108 is a 2D charge-coupled device (CCD) camera. A CCD camera is generally appropriate when a larger field of view or better image quality is desired.

The light source 102 can be a broad spectrum light source that produces electromagnetic radiation 114 in a broad wavelength range that includes any wavelengths necessary for the system (e.g., predefined wavelengths or wavelength components). The wavelength range needed may vary by application, for example depending on what type of sample or object within a sample the imaging target 104 is. For applications that require the electromagnetic radiation to penetrate further, or where the imaging target may be harmed by electromagnetic radiation in the visible wavelength range (between about 390 nm and about 700 nm), larger wavelengths are desirable. This may include organs such as an eye. For applications where the depth penetration of the electromagnetic radiation is not as critical, electromagnetic radiation having smaller wavelengths may be desirable. For example, if the imaging target 104 is a person's internal organ, the internal organ may be accessed using an endoscope or other medical device. In this situation, electromagnetic radiation from light source 102 would not be required to penetrate the user's skin and other material before reaching the internal organ, and instead could be incident directly onto the internal organ. Thus, electromagnetic radiation in a larger wavelength range would not be needed for depth penetration, and electromagnetic radiation in a smaller wavelength range could be utilized to improve resolution.

In accordance with some embodiments of the invention, the light source 102 is preferably selected to be in or include a component having a wavelength range useful for exciting the target fluorophore. Preferably, the light source 102 produces electromagnetic radiation that includes electromagnetic radiation having a predefined wavelength (or wavelength range) that causes the target fluorophore to become excited and emit electromagnetic radiation. In some embodiments of the invention, the light source 102 can include a single supercontinuum laser. In some embodiments of the invention, the light source 102 can include a first light source (e.g. at a first predefined wavelength or wavelength range) used for the OCT imaging, and a second light source (e.g. at a second predefine wavelength or wavelength range) used for the FM imaging. The light source 102 can be an incoherent source producing incoherent electromagnetic radiation.

The electromagnetic radiation 114 produced by the light source 102 propagates along a first optical pathway 110 that is disposed between the light source 102 and the imaging target 104, where the produced electromagnetic radiation 114 is incident on the imaging target. Generally, the produced electromagnetic radiation 114 is incident on the imaging target 104 at an oblique angle, as will be discussed in more detail herein. A first portion of the incident electromagnetic radiation 114 will be reflected by the imaging target 104. The electromagnetic radiation that is reflected is referred to as being in the "reflection wavelength range." Electromagnetic radiation in the reflection wavelength range strikes the sample and is then reflected by structures in the sample. In an embodiment, the reflection wavelength range is between about 550 nanometers (nm) and about 700 nm. This reflected electromagnetic radiation 116 travels along a first portion 113A of a second optical pathway 112 and a second portion 113B of the second optical pathway 112 towards the first imaging device 106. As is shown in FIG. 1, the second optical pathway 112 is disposed between the imaging target 104 and the first image capture device 106. The first optical pathway 110 and the first portion 113A of the second optical pathway 112 can be coaxial such that the two pathways share an optical axis. Electromagnetic radiation propagating along the first portion 113A of the second optical pathway 112 essentially propagates along the first optical pathway 110 in the opposite direction.

Once the reflected electromagnetic radiation 116 reaches the end of the first portion 113A of the second optical pathway 112, the reflected electromagnetic radiation 116 is directed to the second portion 113B of the second optical pathway 112. The reflected electromagnetic radiation 116 then arrives at the first image capture device 106 that utilizes the reflected electromagnetic radiation 116 to obtain a first 3D image of the imaging target 104 using OCT principles. This first 3D image is indicative of structural properties of the sample. The light source 102 and the first image capture device 106 can be appropriate devices for use in various different OCT techniques, such as swept-source OCT, or inverse spectroscopic OCT.

A second portion of the incident electromagnetic radiation 114 is absorbed by the imaging target 104 or fluorophores within the imaging target 104. The electromagnetic radiation that is incident upon the sample and is absorbed by fluorophores in the sample is referred to as being in the "absorption wavelength range." In an embodiment, the absorption wavelength range is between about 420 nm and about 470 nm. Responsive to the second portion of the incident electromagnetic radiation 114 being absorbed, the imaging target 104 or fluorophores within the imaging target 104 emit electromagnetic radiation 118. This emitted electromagnetic radiation 118 is referred to has being in the "emission wavelength range." In an embodiment, the emission wavelength range is between about 485 nm and about 565 nm. This emitted electromagnetic radiation 118 propagates along a third optical pathway 120 toward the second image capture device 108, where it is utilized to obtain a second 3D image of the imaging target 104 using FM principles. This second 3D image is indicative of molecular properties of the imaging target 104.

Figure 2:
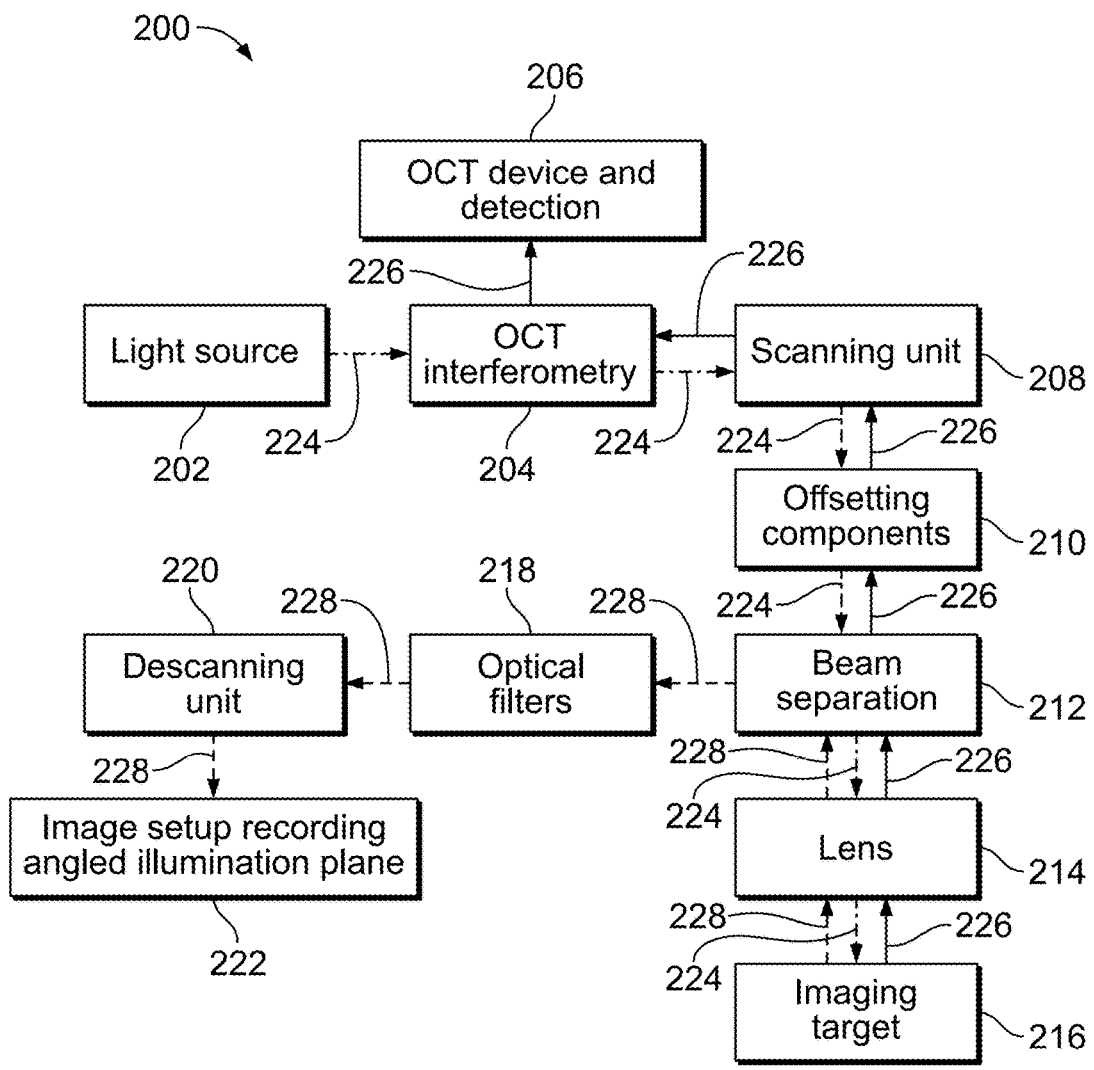
FIG. 2 shows another embodiment of a system for obtaining a three-dimensional image of a sample, according to aspects of the present disclosure.

Referring now to FIG. 2, a system 200 for creating a 3D image of a sample is illustrated. System 200 operates in a manner similar to that of system 100. System 200 includes a light source 202, an imaging target 216, OCT detection equipment 206, and fluorescence detection equipment 222. A first optical pathway is disposed between the light source 202 and the imaging target 216 and includes OCT interferometry equipment 204, a scanning unit 208, a beam offset component 210, a beam separation component 212 and a lens 214. A second optical pathway is disposed between the imaging target 216 and the OCT detection equipment 206 and includes each of these components as well. A third optical pathway is disposed between the imaging target 216 and the fluorescence detection equipment 222, and includes the lens 214, the beam separation component 212, an optical filter 218, and a descanning unit 220.

Light source 202 produces the incident electromagnetic radiation 224 and can be, similar to light source 102, a broad-spectrum light source such as a super continuum laser. OCT interferometry equipment 204 generally includes the equipment for the reference path of the OCT system. OCT interferometry equipment 204 thus includes at least one mirror disposed at an end of the reference path. OCT detection equipment 206 may include the line scan camera that is used to record the reflected electromagnetic radiation 226. Fluorescence detection equipment 222 can be a PMT array or a CCD camera.

The scanning unit 208 is used to steer the incident electromagnetic radiation 224 across the surface of the sample and can include one or more scanning mirrors, such as a galvanometer mirror. Each scanning mirror includes a mirror mounted on a high-precision scanning motor that is capable of moving the mirror in precise increments over a range of angles. The scanning motors are generally configured to rotate the mirror about two different orthogonal axes. Because the scanning motors are able to move the mirrors within a wide range of angle in two different axes, the scanning unit 208 being able to precisely steer the incident electromagnetic radiation 224 across the surface of the sample. The scanning unit can also include other 2D steering devices, such MEMS mirrors.

The beam separation component 212 is used to filter out unwanted wavelength ranges from the incident electromagnetic radiation 224, and to separate the reflected electromagnetic radiation 226 and the emitted electromagnetic radiation 228. It is undesirable for the incident electromagnetic radiation 224 to include electromagnetic radiation in the emission wavelength range. The beam separation component 212 is one mechanism used by the system 200 to ensure that electromagnetic radiation in the emission wavelength range that may be included in the incident electromagnetic radiation 224 does not get transmitted on to the imaging target 216. In accordance with some embodiments of the invention, the beam separation component 212 can include an optical dichroic filter that reflects electromagnetic radiation in the emission wavelength range but transmits electromagnetic radiation in the reflection wavelength range and electromagnetic radiation in the absorption wavelength range. Thus, when the incident electromagnetic radiation 224 strikes the beam separation component 212 before reaching the sample, the beam separation component ensures that electromagnetic radiation in both the reflection wavelength range and the absorption wavelength range is transmitted.

Once the incident electromagnetic radiation 224 has struck the sample, the beam separation component 212 separates out the reflected electromagnetic radiation 226 that will be used for OCT imaging and the emitted electromagnetic radiation 228 that will be used for FM imaging. The reflected electromagnetic radiation 226, being in the reflection wavelength range, will be transmitted through the beam separation component 212 so that it can propagate through the second optical pathway to the OCT interferometry equipment 204 and the OCT detection equipment 206. The emitted electromagnetic radiation 228, being in the emission wavelength range, is reflected by the beam separation component 212 onto the third optical pathway so that the emitted electromagnetic radiation can be used for FM imaging.

The lens 214 can be used to focus the incident electromagnetic radiation 224 on imaging target 216. In an embodiment, the lens 214 is an objective lens. In another embodiment, when the retina is being imaged in vivo, the lens 214 is the lens of the eye being examined.

The beam offset component 210 is used to create an offset between the optical axis of the scanning unit 208 and the optical axis of the lens 214. When the optical axis of the lens 214 is offset, the incident electromagnetic radiation 224 is redirected when passing through the lens 214 such that the incident electromagnetic radiation 224 strikes the imaging target 214 at an oblique angle. In an embodiment, the beam offset component 210 is a dovetail stage or dovetail slider that the beam separation component 212 and the lens 214 are mounted to. A user can use the dovetail stage to precisely position the beam separation component 212 and the lens 214 such that the optical axis thereof is offset from the optical axis of the scanning unit 208. In an embodiment, the offset can be about 4 millimeters (mm). In another embodiment, the offset results in the incident electromagnetic radiation 224 striking the imaging target 214 at an angle of about 26°.

The optical filter 218 acts as an additional filter after the emitted electromagnetic radiation 228 has been separated by the beam separation component 212. The optical filter allows emitted electromagnetic radiation 228 to be transmitted that will be used for the FM imaging. The descanning unit 220 can include one or more scanning mirrors, similar to the scanning unit 208. The descanning unit 220 is used to ensure that the emitted electromagnetic radiation incident on the fluorescence detection equipment 222 provides a stationary image. Finally, the fluorescence detection equipment 222, which is used for the FM imaging, can include a PMT array or a 2D CCD camera.

Figure 3:
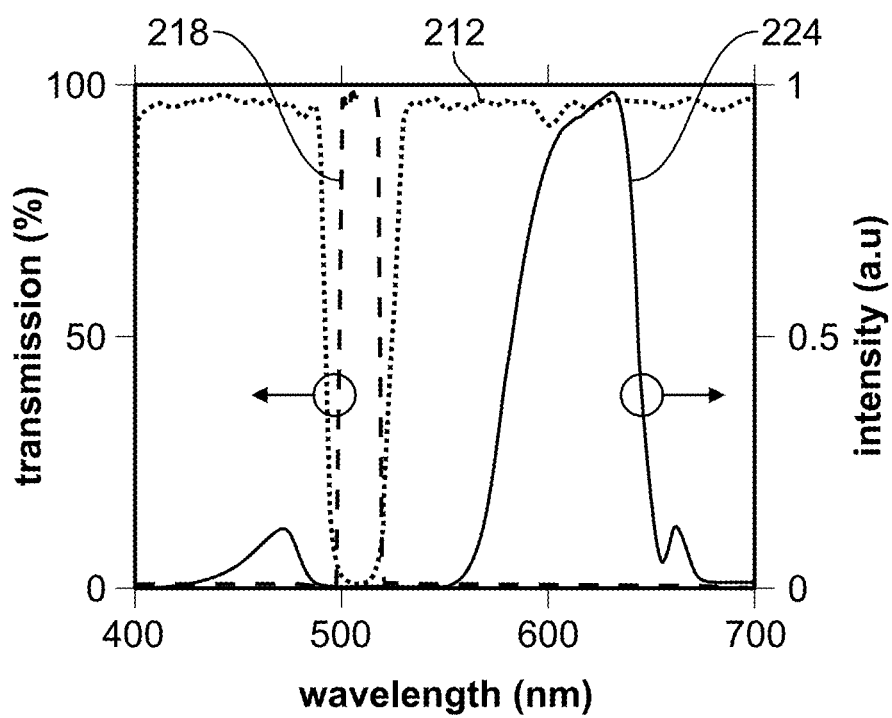
FIG. 3 shows the optical illumination spectrum of electromagnetic radiation incident on a sample, as well as optical transmission spectra of two filters to separate reflected electromagnetic radiation and emitted electromagnetic radiation, according to aspects of the present disclosure.

Referring now to FIG. 3, the illumination spectra of the incident electromagnetic radiation 224 in an embodiment is shown, along with the transmission spectra of the beam separation component 212 and the optical filter 218. As is shown, the incident electromagnetic radiation 224 has a wavelength range of about 420 nm to about 700 nm. The incident electromagnetic radiation 224 is concentrated into two different wavelength ranges. Electromagnetic radiation that is used for OCT purposes has a wavelength from about 550 nm to about 700 nm (the reflection wavelength range). Electromagnetic radiation that is used for FM purposes has a wavelength from about 420 nm to about 470 nm (the absorption wavelength range). The transmission spectra of the beam separation component 212 shows that the beam separation component 212 allows the reflected electromagnetic radiation 226 to pass through, while electromagnetic radiation 228 emitted by fluorophores in the sample are reflected by the beam separation component 212 towards the optical filter 218. In other embodiments, different wavelength ranges for the incident electromagnetic radiation and the emitted electromagnetic radiation are contemplated, as well as different transmission spectra for the beam separation component 212 and the optical filter 218.

Figure 4:
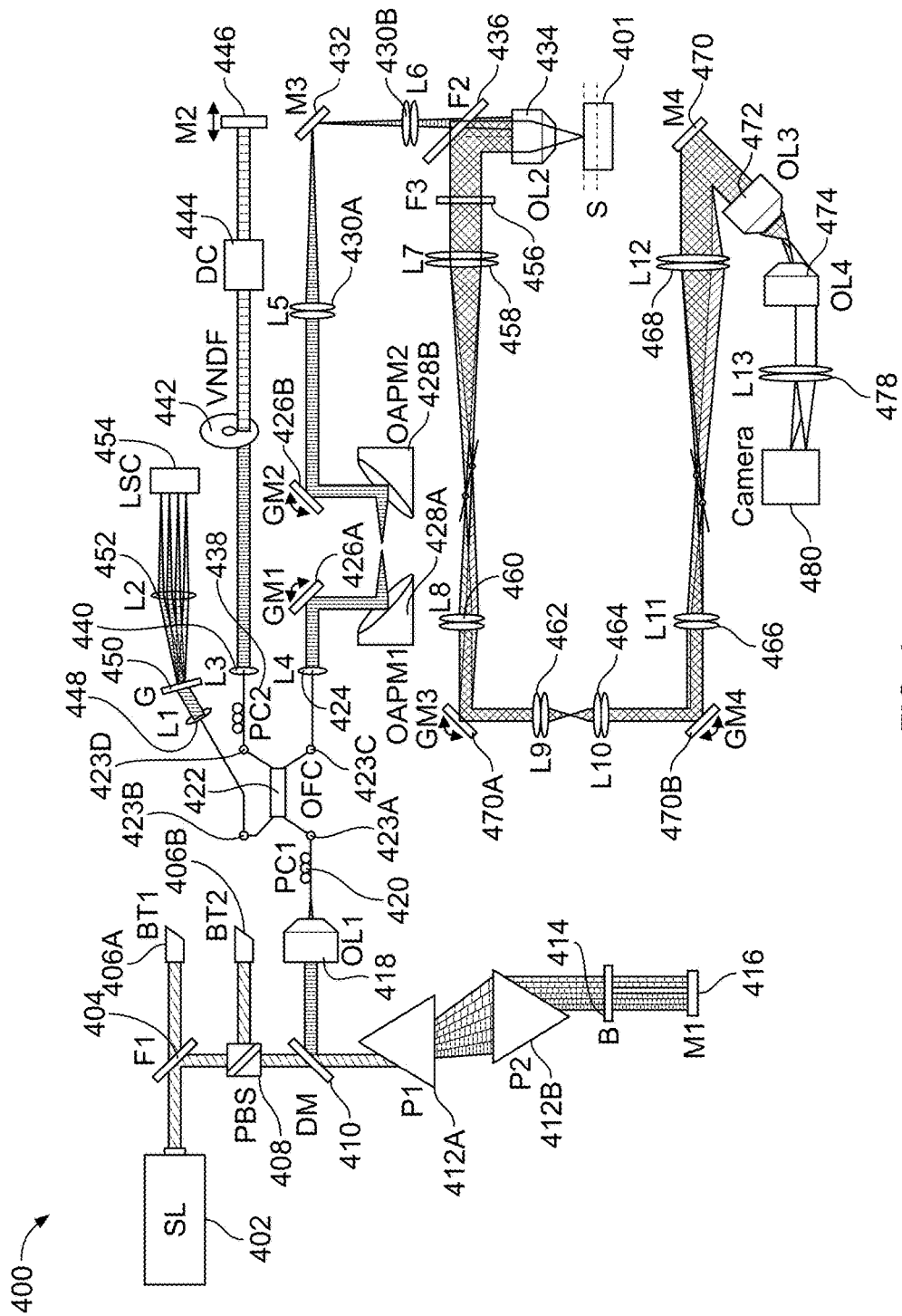
FIG. 4 shows a further embodiment of a system for obtaining a three-dimensional image of a sample, according to aspects of the present disclosure.

Referring now to FIG. 4, a system 400 for obtaining a 3D image of a sample 401 is illustrated. System 400 is a more detailed version of system 200 and operates according to similar principles as system 100 and system 200. System 400 is generally separated into an initial stage, a steering stage, an OCT reference stage, an OCT detection stage, and a fluorescence detection stage. The initial stage includes a light source 402 and various components to prepare the electromagnetic radiation produced by the light source 402. After the electromagnetic radiation is produced, electromagnetic radiation having a wavelength of between about 420 nm and about 650 nm (i.e. light in the visible wavelength range) is transmitted through a filter 404. Electromagnetic radiation in this wavelength range continues to propagate through the system, while the filtered-out light is sent to a beam trap 406A so that the light does not escape from the system and cause harm to people or other components. The remaining produced electromagnetic radiation is then sent through a polarization beam splitter 408 that polarizes the light. The polarization beam splitter 408 effectively selects one polarization of the produced electromagnetic radiation and sends unselected polarizations to a second beam trap 406B. The produced electromagnetic radiation then passes through a D-shaped mirror 410 and a prism system that disperses the produced electromagnetic radiation into separate wavelength components. In an embodiment, the prism system includes a first prism 412A and a second prism 412B. A thin aluminum film 414 is inserted into the path of the produced electromagnetic radiation to block electromagnetic radiation in the emission wavelength range. Thus, the produced electromagnetic radiation at this point primarily includes electromagnetic radiation in the reflection wavelength range and electromagnetic radiation in the absorption wavelength range. The produced electromagnetic radiation is then reflected off of a reflecting mirror 416 and travels back through prisms 412A and 412B, where the separate wavelength components are recombined. The produced electromagnetic radiation is then reflected off of the D-shaped mirror 410 and is collected by an objective lens 418.

At the end of the initial stage, the produced electromagnetic radiation exits the objective lens 418 propagates through a first polarization controller 420. The polarization controller 420 is used to adjust the polarization state of the electromagnetic radiation so that the electromagnetic radiation is properly polarized for use in imaging. After exiting the polarization controller 420, the produced electromagnetic radiation enters an optical fiber coupler 422. In an embodiment, the optical fiber coupler 422 includes a first pair of ports 423A, 423B, and a second pair of ports 423C, 423D. Electromagnetic radiation incident on either port 423A or port 423B of the first pair of ports will be directed to both port 423C and port 423D of the second pair of ports. Similarly, electromagnetic radiation incident on either port 423C or port 423D of the second pair of ports will be directed to both port 423A and 423B of the first pair of ports. In an embodiment, the optical fiber coupler 422 is a 50:50 coupler that outputs electromagnetic radiation incident at either port 423A or 423B at about 50% intensity at both port 423C and port 423D, and vice-versa. In system 400, the produced electromagnetic radiation is incident on port 423A. The produced electromagnetic radiation is output at port 423C to the steering stage, and at port 423D to the reference stage.

The produced electromagnetic radiation that propagates through the steering stage is first collimated by a lens 424. In an embodiment, the lens 424 has a focal length of about 4.5 mm. The produced electromagnetic radiation then propagates through a pair of galvanometer scanning mirrors 426A and 426B, as well as a pair of off-axis parabolic mirrors 428A and 428B. The galvanometer scanning mirrors 426A and 426B are used to scan the produced electromagnetic radiation across the surface of the sample 401. The off-axis parabolic mirrors 428A and 428B are used to minimize or eliminate chromatic aberration. Chromatic aberration can occur when different wavelengths of electromagnetic radiation (i.e. different colors of light) are focused at different distances from the lens 424 along the optical axis of the steering stage. This can occur where the lens 424 is not able to focus all wavelength of electromagnetic radiation at the same point due to the lens 424 having different refractive indices for different wavelengths of electromagnetic radiation. The off-axis parabolic mirrors 428A and 428B are used to correct for these focusing errors. If the chromatic aberration due to the lens 424 is negligible, the off-axis parabolic mirrors 428A and 428B can be replaced by a standard optical relay system.

After propagating through the galvanometer scanning mirrors 426A and 426B, and the off-axis parabolic mirrors 428A and 428B, the produced electromagnetic radiation propagates through lens 430A, mirror 432, and lens 430B. Lens 430A, mirror 432, and lens 430B are arranged in a telescope system that directs the produced electromagnetic radiation to the back pupil of an objective lens 434. Lenses 430A and 430B of the telescope system can each be an achromatic doublet so as to reduce spherical aberration and astigmatism. An optical filter 436 is disposed in the optical pathway of the steering stage between the lens 430B of the telescope system and the objective lens 432. The optical filter 436 allows electromagnetic radiation in the reflection wavelength range and the absorption wavelength range to be transmitted through the optical filter 436 where can be collected by the objective lens 434.

The objective lens 434 and the optical filter 436 may be mounted on a dovetail stage or dovetail slider to adjust an offset between (i) an optical axis of those components; and (ii) an optical axis of the telescope system including lens 430A, mirror 432, and lens 430B. Because of this offset, the produced electromagnetic radiation collected by the objective lens 434 is output from the objective lens 434 at an angle such that the produced electromagnetic radiation is incident on the surface of the sample 401 at an oblique angle. After the produced electromagnetic radiation strikes the sample 401, a portion of the produced electromagnetic radiation is reflected and a portion of the electromagnetic radiation is absorbed. The portion of the produced electromagnetic radiation that is reflected is generally in a first wavelength range. In an embodiment, the first wavelength range is between about 550 nm and about 700 nm. The portion of the produced electromagnetic radiation that is absorbed is generally in a second wavelength range. In an embodiment, the second wavelength range is about 420 nm to about 470 nm. The sample 401 emits a certain amount of electromagnetic radiation in response to the absorption. The emitted electromagnetic radiation is generally in a third wavelength range. In an embodiment, the third wavelength range is between about 485 nm and about 565 nm. The reflected electromagnetic radiation and the emitted electromagnetic radiation then strike the optical filter 436. The optical filter 436 allows the reflected electromagnetic radiation to be transmitted through the optical filter 436 and propagate back through the steering stage, while the optical filter redirects the emitted electromagnetic radiation to the fluorescence detection stage. The reflected electromagnetic radiation propagates back through the steering stage until it enters port 423C of the optical fiber coupler 422. The optical fiber coupler 422 then outputs the reflected electromagnetic radiation to the OCT detection stage at port 423B.

The reference stage is used as the reference arm for OCT imaging. The produced electromagnetic radiation incident on port 423A is output at port 423D to the reference stage. The produced electromagnetic radiation propagates through a second polarization controller 438. The polarization controller 438 is configured to ensure that the polarization of the electromagnetic radiation propagating through the reference stage is identical to the polarization of the electromagnetic radiation propagating through the steering stage. The produced electromagnetic radiation is then collimated by a lens 440 and directed to a variable neutral density filter 442 to attenuate the power of the electromagnetic radiation propagating through the reference stage. This attenuation ensures that that the OCT detection equipment is not oversaturated. The produced electromagnetic radiation then propagates through a dispersion compensator 444 to compensate for any dispersion introduced to the electromagnetic radiation propagating through the steering stage by the optical equipment in the steering stage. Finally, the produced electromagnetic radiation reflects off of a mirror 446 and propagates back through the reference stage until it reaches port 423D of the optical fiber coupler 422. The electromagnetic radiation from the reference stage is then output at port 423B of the optical fiber coupler 422 to the OCT detection stage.

Both the reflected electromagnetic radiation from the steering stage and the reference electromagnetic radiation from the reference stage are output at port 423B of the optical fiber coupler 422 to the OCT detection stage. Both beams of electromagnetic radiation are collimated by a lens 448. The electromagnetic radiation then propagates through a grating 450, and another lens 452. The grating 450 disperses the reflected electromagnetic radiation and the reference electromagnetic radiation into a spectrum by reflecting different wavelengths or wavelength components at different angles. This spectrum can be used to create the interference pattern and determine the structural properties of the sample 401. Finally, the electromagnetic radiation is focused onto a line scan camera 454 by the lens 452. The line scan camera 452 is used to create an image of the sample 401. In accordance with other embodiments of the invention, alternative OCT detection schemes can be used, such as swept-source OCT.

The electromagnetic radiation emitted by the sample 401 is collected by the objective lens 434 and is reflected into the fluorescence detection stage by the optical filter 436. This emitted electromagnetic radiation passes through an optical band-pass filter 456 to ensure that only electromagnetic radiation in the emission wavelength range is detected by the fluorescence microscopy equipment. The emitted electromagnetic radiation then propagates through multiple telescope systems. The first telescope system includes lens 458 and lens 460. The second telescope system includes lens 462 and lens 464. The third telescope system includes lens 466 and 468. Each lens in the three telescope systems can be an achromatic doublet lens to reduce spherical aberration and astigmatism. A first galvanometer scanning mirror 470A is disposed between the first telescope system and the second telescope system. A second galvanometer scanning mirror 470B is disposed between the second telescope system and the third telescope system. The two galvanometer scanning mirrors 470A and 470B are used to ensure that the emitted electromagnetic radiation incident on the fluorescence detection equipment provides a stationary image. The three telescope systems increase the field of view of the fluorescence detection equipment.

After propagating through the lens 468 of the third telescope system, the emitted electromagnetic radiation is reflected off of a mirror 470 and gathered by an objective lens 472. Mirror 470 can be utilized to ease alignment of the emitted electromagnetic radiation with the fluorescence detection equipment. The objective lens 472 can be used to create a conjugate space to the sample space, and to change the angle of the image if necessary. The magnification of the fluorescence detection stage between the objective lens 434 that gathers the emitted electromagnetic radiation from the sample 401 and the objective lens 472 that gathers that emitted electromagnetic radiation after it travels through the telescope systems is about ⅔. Finally, an imaging system is used to project the emitted electromagnetic radiation to the image capture device. In FIG. 4, the imaging system to project the emitted electromagnetic radiation to the image capture device includes an objective lens 474 and another lens 478. These components can be used to refocus the tilted image in the conjugate plane after the electromagnetic radiation propagates through objective lens 427. After the emitted electromagnetic radiation propagates through these components, it is incident on image capture device 480, which can be a CCD camera. The CCD camera 480 is used to construct the 3D image of the sample 401 via fluorescence microscopy principles.

Figure 5:
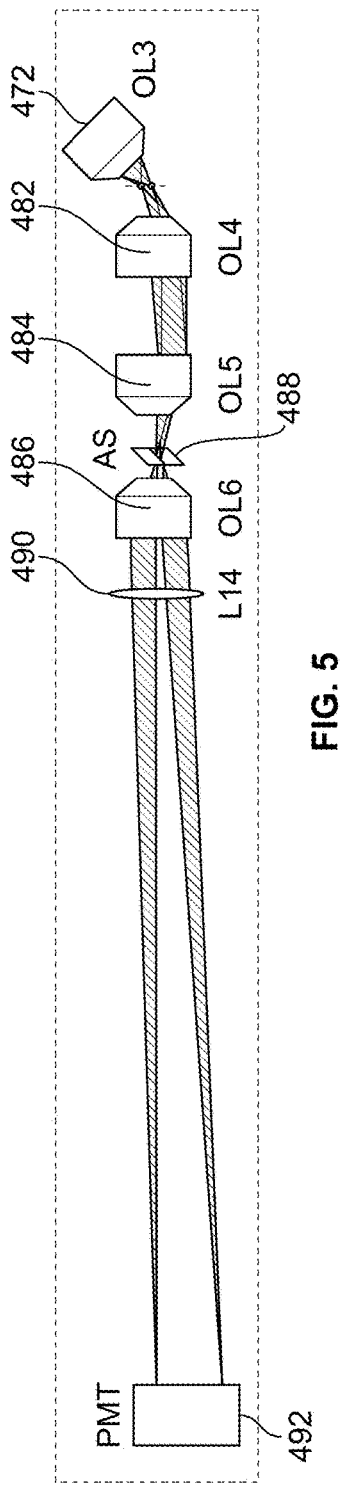
FIG. 5 shows an embodiment of a system that utilizes a photomultiplier tube array to detect emitted electromagnetic radiation, according to aspects of the present disclosure.

FIG. 5 illustrates this imaging system when a PMT array is used to capture the fluorescence image rather than the CCD camera. FIG. 5 also shows the objective lens 472 leading to the imaging system. The imaging system includes a first objective lens 482, a second objective lens 484, and a third objective lens 486. An adjustable slit 488 is disposed between the second objective lens 484 and the third objective lens 486. After exiting the third objective lens 486, the emitted electromagnetic radiation passes through lens 490 and is then incident on image capture device 492, which can be a PMT array. The objective lens 482, 484, and 488, as well as lens 486 are used to magnify the image in two steps, which can avoid using a focusing lens with a very large focal length with the PMT array 492, which is significantly larger than the CCD camera 480. Moreover, the use of these lenses allows for the installation of an adjustable slit, which can be used for confocal gating.

Figure 6:
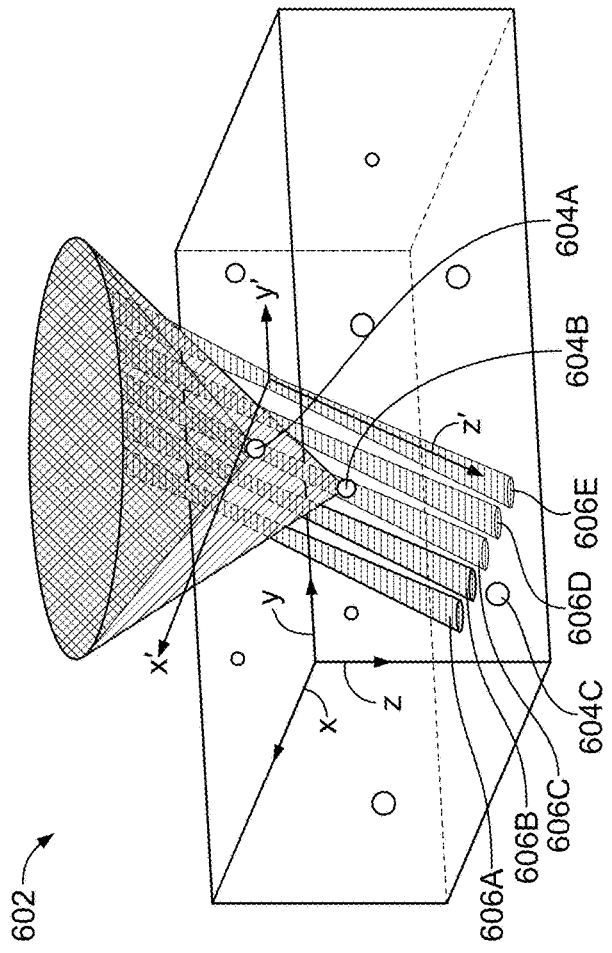
FIG. 6 shows a three-dimensional representation of a sample being illuminated by electromagnetic radiation, according to aspects of the present disclosure.

Referring now to FIG. 6, an exemplary view of a sample 602 being illuminated with incident electromagnetic radiation and emitting electromagnetic radiation is shown. As can be seen, the sample 602 includes a number of different structures embedded within the sample itself. For example, the sample 602 includes at least structures 604A, 604B, and 604C that are in the path of the incident electromagnetic radiation. The incident electromagnetic radiation is represented by five beams 606A-606E. The standard reference frame for the sample 602 is shown by the axis labels x, y, and z. The five beams of electromagnetic radiation 606A-606E are incident on the sample 602 at an oblique angle. The incident electromagnetic radiation is thus parallel to axis z', which is at an oblique angle when compared to normal axis z. The beams of incident electromagnetic radiation 606A-606E are shown illuminating structures 604A and 604B, which are highlighted in green. When the fluorophores in these structures absorb the incident electromagnetic radiation that is in the absorption wavelength range, they emit electromagnetic radiation in the emission wavelength range. This emitted electromagnetic radiation is shown by the green triangles emanating upwards from structures 604A and 604B.

This emitted electromagnetic radiation is collected and sent to a CCD camera or a PMT array. In normal FM imaging, the sample would have to be scanned at different depths along the z axis, in addition to scanning across the x and y axes, in order to create the 3D image. However, by scanning the incident electromagnetic radiation on the sample at an oblique angle, structures at different locations within the x-y plane are illuminated. By measuring the electromagnetic radiation emitted from the illuminated structures from overhead, i.e. a 0° angle, the system is able to differentiate between electromagnetic radiation emitted from one structure and electromagnetic radiation emitted from a structure deeper in the sample, because the structure deeper in the sample is at a different location in the x-y plane. As such, the oblique angle of incidence allows the system to obtain fluorescence information about structures at different depths within the sample without having to specifically scan the sample at different depths.

With respect to the OCT imaging, electromagnetic radiation reflected off of structures within the sample is collected by the line scan camera. By capturing electromagnetic radiation reflected off of each structure disposed along the z' axis for any given point in the x-y plane, and comparing that captured electromagnetic radiation to electromagnetic radiation from the reference arm of the OCT system, the system is able to construct an interferogram. This interferogram shows interference patterns between the electromagnetic radiation from the reference arm and the captured electromagnetic radiation reflected off of the structures in the sample, which can then be used to construct an image of the structures along the z' axis.

Referring now to FIGS. 7A and 7B, longitudinal cross sections of the incident electromagnetic radiation as it is scanned across the surface of the sample are illustrated. FIG. 7A shows cross-sectional images in the x-z plane, referring to the coordinate axes shown in FIG. 6. As the oblique angle tilts the incident electromagnetic radiation in the y-z plane, the cross-sectional images in the x-z plane simply show the incident electromagnetic radiation as a vertical line at various positions along the x-axis. In contrast, the cross-sectional images in the y-z plane shown in FIG. 7B show the oblique angle of the incident electromagnetic radiation for various positions along the y-axis.

Figure 8:
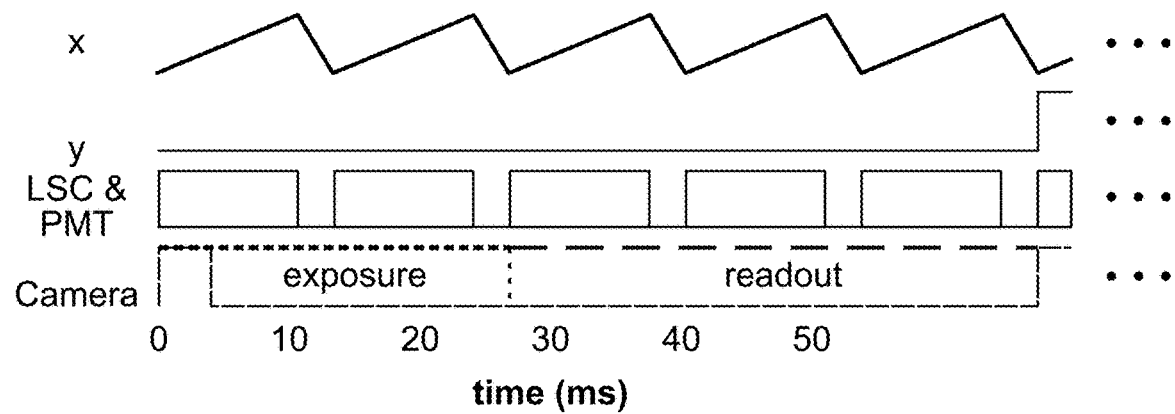
FIG. 8 shows the timing of the scanning of the incident electromagnetic radiation on the sample, as well as the triggering of a line scan camera, a photomultiplier tube array, and a CCD camera, according to aspects of the present disclosure.

Referring now to FIG. 8, the x and y locations of the incident electromagnetic radiation on the sample versus time is illustrated. This diagram also shows when the line scan camera is activated for the OCT imaging, and when either the PMT array or the CCD camera is activated for the FM imaging. As shown, the system scans the incident electromagnetic radiation along the x-axis of the sample in a saw-tooth pattern, multiple times for a discrete location along the y-axis of the sample. The incident electromagnetic radiation is scanned faster in the x-direction than the y-direction. The x-direction is thus referred to as the "fast-scanning direction," while the y-direction is referred to as the "slow-scanning direction." In an embodiment, the system controls the scanning in the fast-scanning direction by using a saw-tooth voltage with an 80% duty cycle. In an embodiment, the system scans the incident electromagnetic radiation along the fast-scanning direction five times while the y-direction is held constant. Following these five scans, the system then steers the incident electromagnetic radiation a discrete distance in the slow-scanning direction to another discrete location, where the system again scans the incident electromagnetic radiation along the fast-scanning direction. In other embodiments, the system may scan the incident electromagnetic radiation a different number of times along the fast-scanning direction for each location along the slow-scanning direction.

For the OCT imaging, the line scan camera is active and capturing reflected radiation while the system scans the incident electromagnetic radiation along the fast-scanning direction. When the system has completed one scan along the fast-scanning direction and is returning to the initial location along the fast-scanning direction, the line scan camera deactivates and does not capture any reflected electromagnetic radiation. The line scan camera then activates again once the system begins scanning again along the fast-scanning direction. When the PMT array is used for the FM imaging, the PMT array follows the same activation pattern as the line scan camera. When a CCD camera is used for the FM imaging, a single trigger is given to the CCD camera at the beginning of the fast-scanning process at each location along the slow-scanning direction. In an embodiment, the exposure time of the camera lasts for two scans in the fast-scanning direction at each location along in the slow-scanning direction. The camera collects the emitted electromagnetic radiation from the sample during the exposure time.

In an embodiment, frequency for each single scan along the fast-scanning direction is about 50 kHz. In this embodiment, the line scan camera and the PMT array both operate at 50 kHz. In an embodiment, the CCD camera exposure time is about 20 milliseconds. The maximum frame rate for the line scan camera and the PMT array is approximately 100 frames per second. The maximum frame rate for the CCD camera is approximately 20 frames per second. Systems 100, 200, and 400 provide a resolution for OCT imaging of approximately 7.0 micrometers (μm)×7.0 μm×3.5 μm. The resolution of the FM imaging is approximately 3.6 μm×4.2 μm×6.5 μm. The overall imaging rate is about 100 frames per second over a volume of about 1.0×0.8×0.4 mm$^3$.

Figure 9:
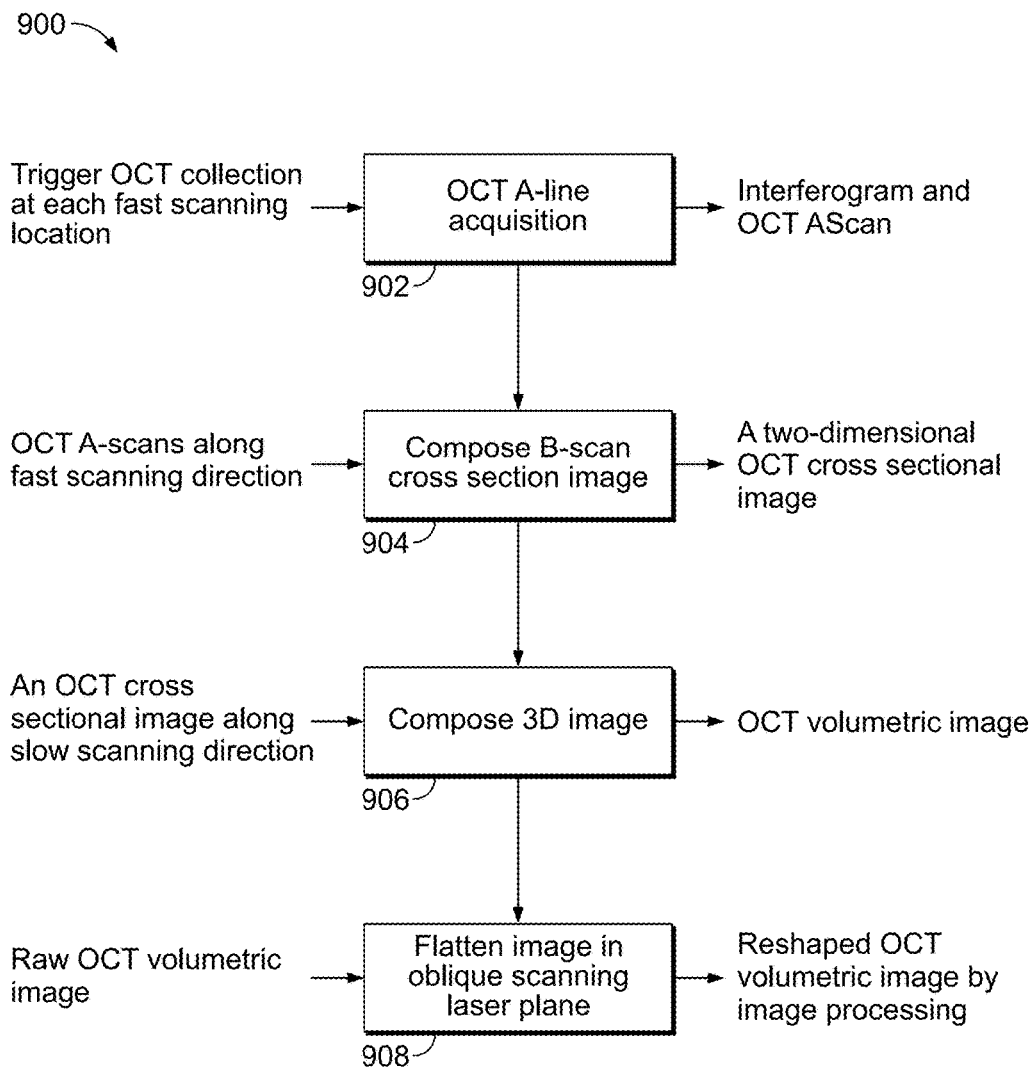
FIG. 9 shows a method for constructing a three-dimensional image of a sample using optical coherence tomography techniques, according to aspects of the present disclosure.

Referring now to FIG. 9, a method 900 for constructing the 3D OCT images is shown. At step 902, the system acquires the OCT A-line scans. Here, the system triggers the line scan camera to capture light reflected from the sample along the tilted depth direction at any point on the surface of the sample, i.e. along the z' axis for any point in the x-y plane, as shown in FIG. 6. An A-line scan is then created from the captured reflected electromagnetic radiation, which shows structures at different depths within the sample along the z' axis at any given point on the sample. This A-line scan can be shifted an incremental distance to compensate for the oblique angle of incidence. Additionally, alternatively, or optionally, the image can be shifted after multiple A-line scans have been captured and formed into a cross-sectional image. At step 904, the system scans the incident electromagnetic radiation across the surface of the sample in the fast-scanning direction. This captures an OCT A-line scan at multiple points along the fast-scanning axis, which can be the x-axis. These multiple A-line scans are combined, which results in a 2D cross-sectional image of the sample in the oblique scanning plane, which can be the x-z plane. This 2D cross-sectional image is known as the B-scan.

At step 906, a raw OCT volumetric image of the sample is formed by scanning the incident electromagnetic radiation across the surface of the sample in the fast-scanning direction for multiple locations in the slow-scanning direction. Here, the system captures multiple cross-section images in the x-z plane (or B-scans) and combines them into a single 3D image. At step 908, the raw OCT volumetric image is adjusted to compensate for the oblique angle of incidence of the incident electromagnetic radiation. Because of the oblique angle of incidence, cross-sectional images of the raw OCT volumetric image in the y-z plane show structures in the surface being tilted towards the y'-z' plane. To correct for this tilt, the z-dimension of the raw OCT volumetric image is shifted until the image is flattened or re-shaped. Additionally, alternatively, or optionally, each A-line scan can be shifted up an incremental distance such that the tilted surface appears flat. The completed 3D OCT image of the sample is thus formed. Once the completed 3D FM image has been formed, the two sets of 3D images can be co-registered to create a single 3D image of the sample. In an embodiment, the cross-sectional images are first combined to form the 3D OCT image and then adjusted to compensate for the oblique angle of incidence. In another embodiment, the cross-sectional images are first adjusted to compensate for the oblique angle of incidence and then combined to form the 3D OCT image.

Figure 10:
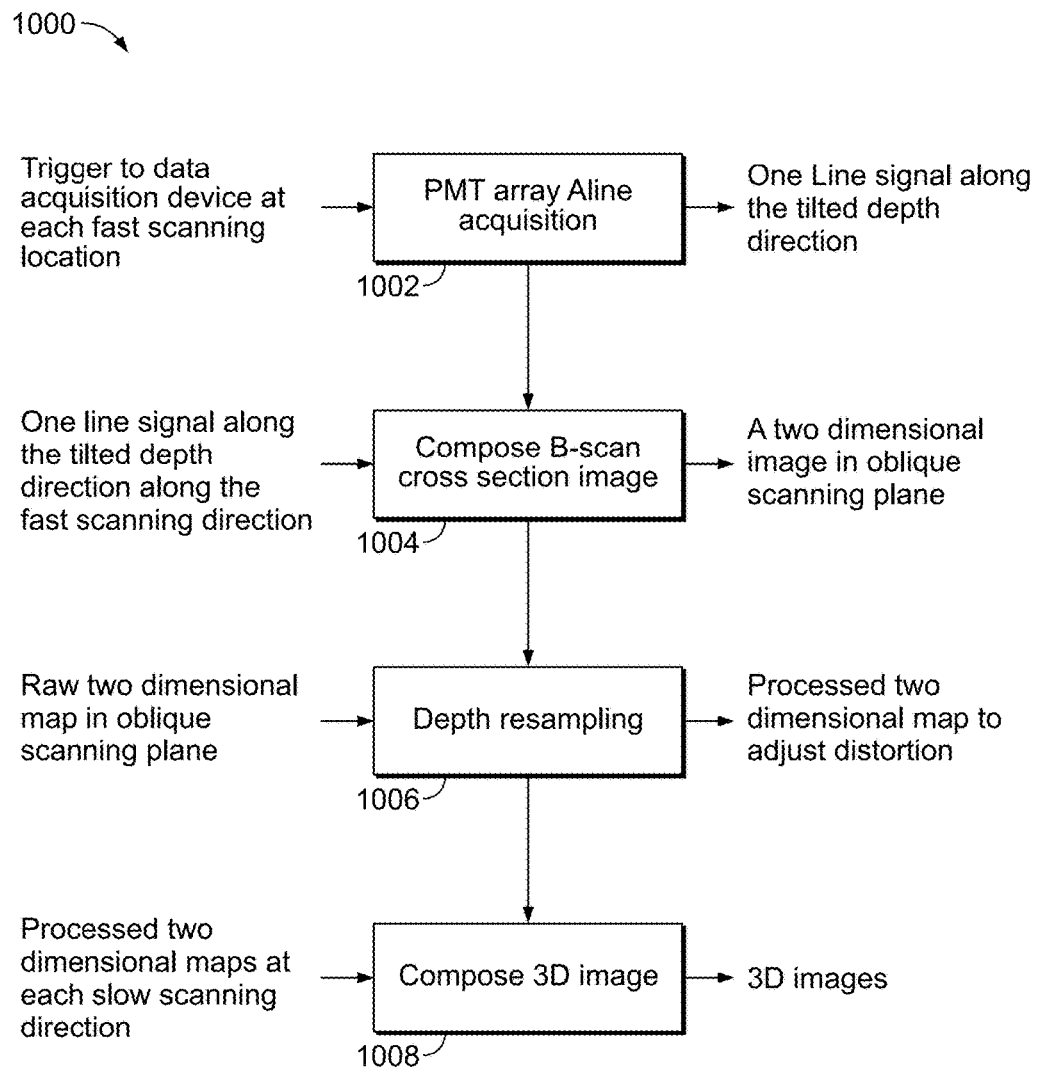
FIG. 10 shows a method for constructing a three-dimensional image of a sample using fluorescence microscopy techniques, according to aspects of the present disclosure.

Referring now to FIG. 10, a method 1000 for constructing 3D FM images with a PMT array is shown. At step 1002, the system acquires the FM A-line scans. The system triggers the PMT array to capture electromagnetic radiation emitted by the fluorophores in the sample when they absorb a portion of the incident electromagnetic radiation. Using the principles discussed in connection with FIG. 6, the system is able to capture an A-line scan of the sample showing fluorescence information for structures at different depths within the sample, without having to re-scan the sample at different depths. At step 1004, the system scans the incident electromagnetic radiation across the surface of the sample in the fast-scanning direction. This captures an FM A-line scan along the tilted z' axis at multiple points along the fast-scanning axis, which can be the x-axis. These multiple A-line scans are combined, which results in a 2D cross-sectional image of the sample in the oblique scanning plane. This 2D cross-sectional image is the B-scan for the FM imaging. At step 1006, the 2D cross-sectional image (or B-scan) is re-sampled to compensate for the apparent depth of the different structures due to the oblique angle of incidence. This re-sampling determines the actual depth of various structures that appear in the B-scan and creates a processed B-scan. At step 1008, multiple processed B-scans are combined to create the 3D FM image of the sample. In an embodiment, the cross-sectional images are first combined to form the 3D FM image and then adjusted to compensate for the oblique angle of incidence. In another embodiment, the cross-sectional images are first adjusted to compensate for the oblique angle of incidence and then combined to form the 3D FM image. The 3D FM image of the sample from the PMT array can then be co-registered with the 3D OCT image to create a single 3D image of the sample.

Figure 11:
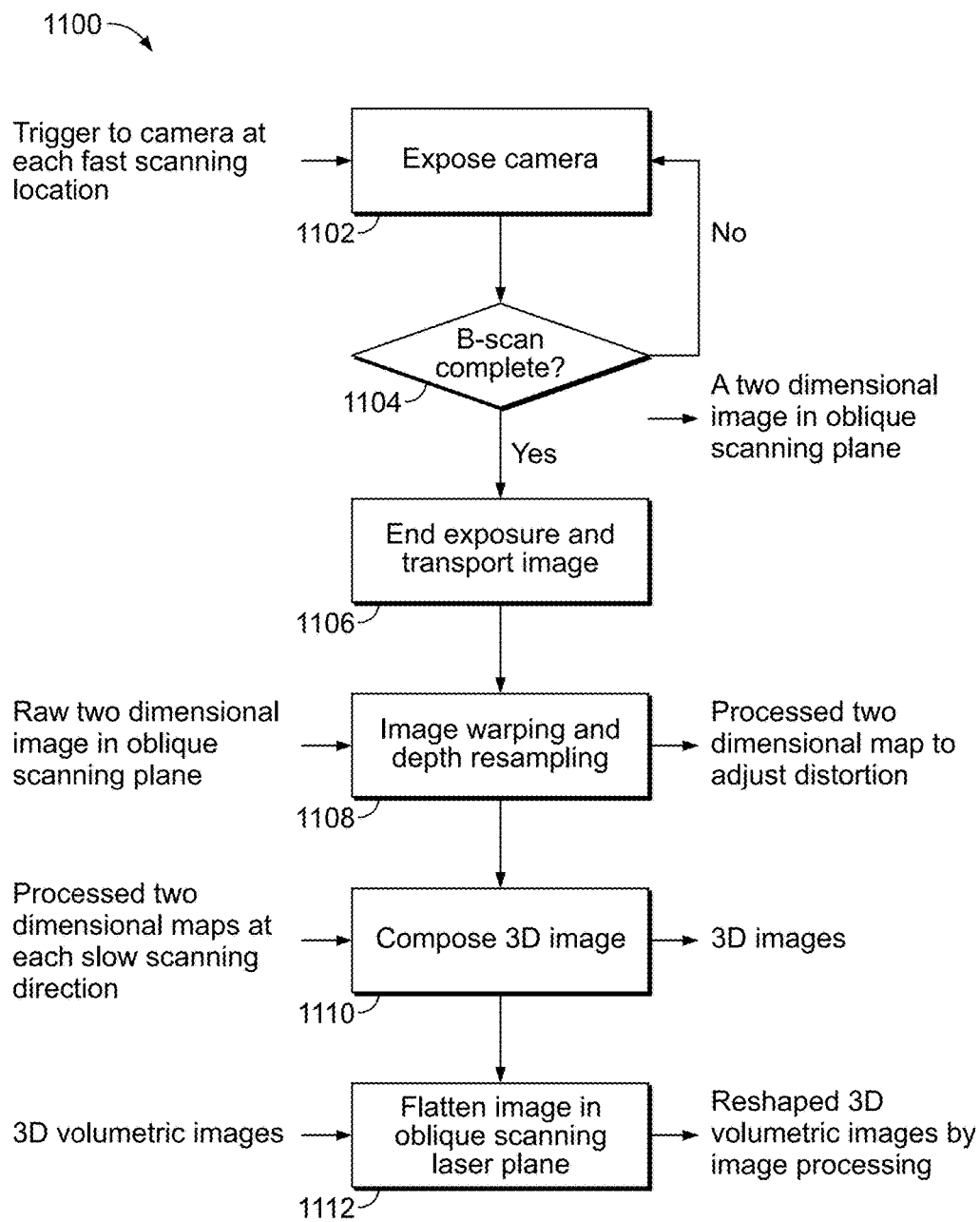
FIG. 11 shows another method for constructing a three-dimensional image of a sample using fluorescence microscopy techniques, according to aspects of the present disclosure.

Referring now to FIG. 11, a method 1100 for constructing 3D FM images with a CCD camera is shown. At step 1102, the CCD is camera is triggered to begin collected emitted electromagnetic radiation. At step 1104, the system determines whether or not a B-scan has been completed. If a B-scan has been completed, i.e. if the system has fully scanned the incident electromagnetic radiation along the fast-scanning direction, the CCD camera is turned off at step 1106 while the system moves the incident electromagnetic radiation to the next discrete location along the slow-scanning axis. A B-scan at each discrete location along the slow-scanning axis is collected. The B-scans are 2D cross-sectional images of the sample. If the B-scan has not been completed, the CCD camera continues to collect emitted electromagnetic radiation.

At step 1108, the 2D cross-sectional images of the sample are processed to compensate for the tilted depth direction. This processing includes warping the images and then re-sampling the images to determine the actual depth of various structures that appear in images. At step 1110, the multiple processed 2D cross-sectional images for each location along the slow-scanning axis are combined to create a 3D FM image. Similar to the OCT image, the 3D FM image captured by the CCD camera shows structures being tilted towards the y'-z' plane. To correct for this tilt, at step 1112 the z-dimension of the 3D image is shifted until the image is flattened or re-shaped. In an embodiment, the cross-sectional images are first combined to form the 3D FM image and then adjusted to compensate for the oblique angle of incidence. In another embodiment, the cross-sectional images are first adjusted to compensate for the oblique angle of incidence and then combined to form the 3D FM image. The 3D FM image of the sample from the CCD camera can then be co-registered with the 3D OCT image to create a single 3D image of the sample.

Figure 12:
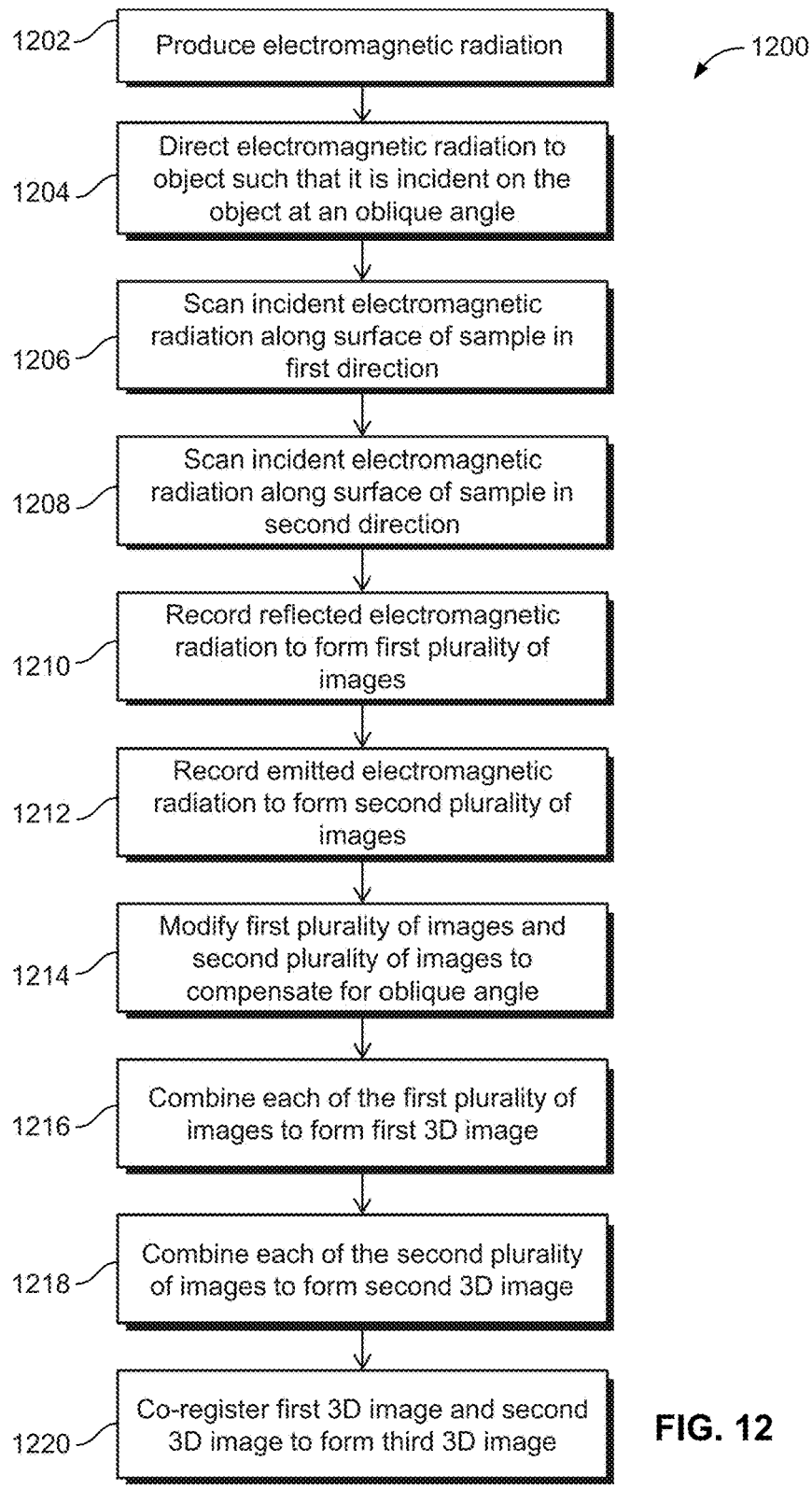
FIG. 12 shows a method for constructing a three-dimensional image of a sample using both optical coherence tomography techniques and fluorescence microscopy techniques, according to aspects of the present disclosure.

Referring now to FIG. 12, a method 1200 of obtaining a 3D image of a sample is illustrated. At step 1202, a broad-spectrum electromagnetic radiation source produces electromagnetic radiation. At step 1204, the produced electromagnetic radiation is directed towards a sample such that the produced electromagnetic radiation is incident on the sample at an oblique angle. The incident electromagnetic radiation is configured such that the sample reflects a first portion of the incident electromagnetic radiation to produce reflected electromagnetic radiation. The incident electromagnetic radiation is also configured such that the sample absorbs a second portion of the incident electromagnetic radiation, and responsive to this absorption, emits electromagnetic radiation.

At step 1206, the incident electromagnetic radiation is scanned across a surface of the sample in a first direction. The incident electromagnetic radiation is scanned in discrete increments to a plurality of discrete locations on the surface of the sample. At step 1208, for each discrete location on the surface of the sample, the incident electromagnetic radiation is scanned across the surface of the sample in a second direction orthogonal to the first direction. At step 1210, electromagnetic radiation reflected by the sample is recorded while the incident electromagnetic radiation is scanned across the surface of the sample to obtain a first plurality of cross-sectional images. At step 1212, electromagnetic radiation emitted by the sample is recorded while scanning the incident electromagnetic radiation across the surface of the sample to produce a second plurality of cross-sectional images of the sample.

At step 1214, each cross-sectional image of the first and second plurality of cross-sectional images of the sample is modified to compensate for the oblique angle of the incident electromagnetic radiation. At step 1216, the cross-sectional images of the first plurality of modified cross-sectional images are combined to create a first 3D image of the sample. At step 1218, the cross-sectional images of the second plurality of modified cross-sectional images are combined to create a second 3D image of the sample. Alternatively, steps 1216 and 1218 can be performed prior to step 1214. In this embodiment, the cross-sectional images of the first plurality of cross-sectional images are combined to form a first 3D image of the sample, and the cross-sectional images of the second plurality of cross-sectional images are combined to form a second 3D image of the sample. Both the first 3D image and the second 3D image can then be modified to compensate for the oblique angle of the incident electromagnetic radiation. Finally, at step 1220, the first 3D image of the sample and the second 3D image of the sample are co-registered to create a third 3D image of the sample.

Referring now to FIGS. 13-16B, the results of a calibration procedure determining the steps needed to compensate for the oblique angle of the incident electromagnetic radiation are shown. FIG. 13 shows the resulting 3D image of a sample. The sample includes a four-layer fluorescein solution mixed with 0.08 μm beads. The four-layer structure of the sample was formed by sandwiching the solution between a glass slide and four cover slips. The depth of the sample is known, as each coverslip has a thickness of about 150 μm. Using this information, the layers in the solution are assigned a depth of 0 μm, 150 μm, 300 μm, and 450 μm.

FIG. 14A illustrates the initial OCT cross-sectional images in the y-z plane. Due to the oblique angle of the incident electromagnetic radiation, the four horizontal surfaces appear tiled about the x axis. FIG. 14B illustrates the cross-sectional images after they have been warped to correct for the oblique angle of the incident electromagnetic radiation. As the structure of the four-layer fluorescein solution is known beforehand, the z-dimension of the cross-sectional images can be shifted until the horizontal surfaces are flattened or re-shaped and the cross-sectional images represent the actual structures in the sample. The parameters of this shift can then be used with future samples where the structure of the sample is not known beforehand.

FIG. 15A shows the initial FM cross-sectional images in the x-z plane. Due to the oblique angle of incidence and because the resulting images from different depths within the sample have different magnifications, the horizontal surfaces appear in a trapezoid-like shape. FIG. 15B shows the warping of these cross-sectional shapes to transfer the trapezoid-like shape to a rectangular shape. As the structure of the four-layer fluorescein solution is known, the image is warped until the image matches what is known about the sample. An interpolation operation was also performed on the cross-sectional images from the x-z plane to adjust the distance between the horizontal surfaces in the cross-sectional images to obtain a linear depth scale. Because of the oblique angle of incidence, the distance between the layers appears greater than it actually is and the images have a non-linear depth scale. Because the depth of each of the fluorescent layers is known and is on a linear scale, an interpolation is performed to resample the depth dimension to produce an image that has a linear scale. The parameters of these interpolations can then be used with future samples where the structure of the sample is not known beforehand.

FIGS. 16A and 16B illustrate further image processing done on FM cross-sectional images in the y-z plane. Again, interpolation operations were performed on the cross-sectional images from the y-z plane to adjust the distance between the horizontal surfaces based on the known distances between the layers of the structures in the sample. Thus, the parameters of the shifts and the interpolations needed to compensate for the oblique angle of incidence can be determined from this calibration procedure. Those determined parameters can then be used with future samples where the structure of the sample is not known beforehand.

Figure 17:
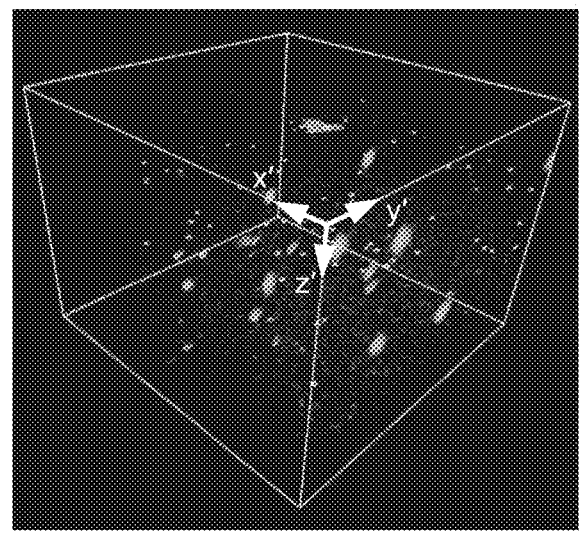
FIG. 17 shows a three-dimensional image of a solution containing fluorescent and non-fluorescent microspheres, according to aspects of the present disclosure.

The application of these methods for simultaneous 3D imaging of an unknown sample is shown in FIGS. 17-20C. FIG. 17 shows a 3D image of a sample that was imaged according to the techniques disclosed herein. The sample includes a mixture of fluorescent and non-fluorescent microspheres sealed in Agarose gel. The OCT imaging techniques are able to produce images of both types of microspheres, as well as a dust particle that was trapped in the sample. The FM imaging techniques can show the molecular specificity of the fluorescent microspheres.

Figure 18A:
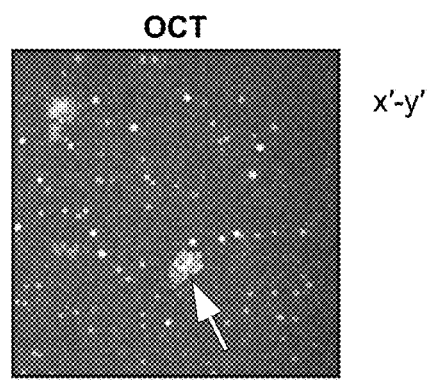
FIG. 18A shows an x-y cross section of the solution of FIG. 17 captured using optical coherence tomography techniques, according to aspects of the present disclosure.
Figure 18B:
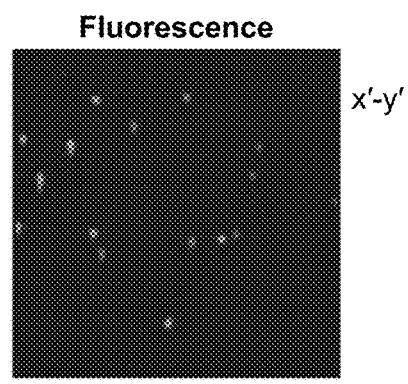
FIG. 18B shows an x-y cross section of the solution of FIG. 17 captured using fluorescence microscopy techniques, according to aspects of the present disclosure.
Figure 18C:
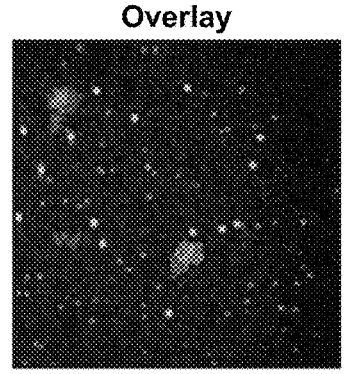
FIG. 18C shows the x-y cross sections of FIG. 18A and FIG. 18B overlaid on top of each other.
Figure 19A:
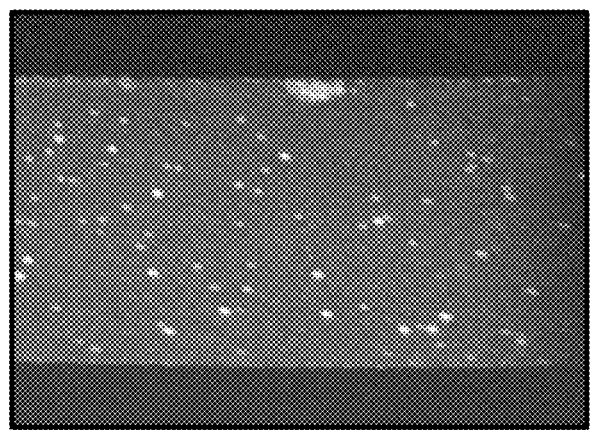
FIG. 19A shows an x-z cross section of the solution of FIG. 17 captured using optical coherence tomography techniques, according to aspects of the present disclosure.
Figure 19B:
FIG. 19B shows an x-z cross section of the solution of FIG. 17 captured using fluorescence microscopy techniques, according to aspects of the present disclosure.
Figure 19C:
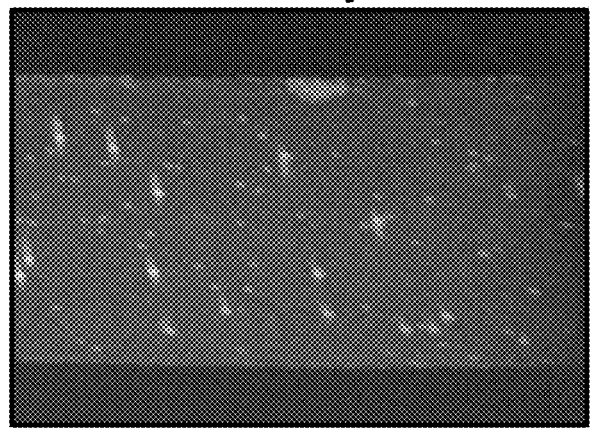
FIG. 19C shows the x-z cross sections of FIG. 19A and FIG. 19B overlaid on top of each other.
Figure 20A:
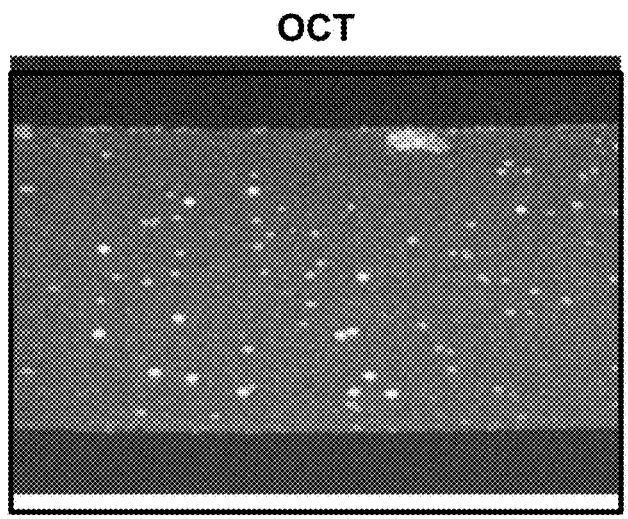
FIG. 20A shows a y-z cross section of the solution of FIG. 17 captured using optical coherence tomography techniques, according to aspects of the present disclosure.
Figure 20B:
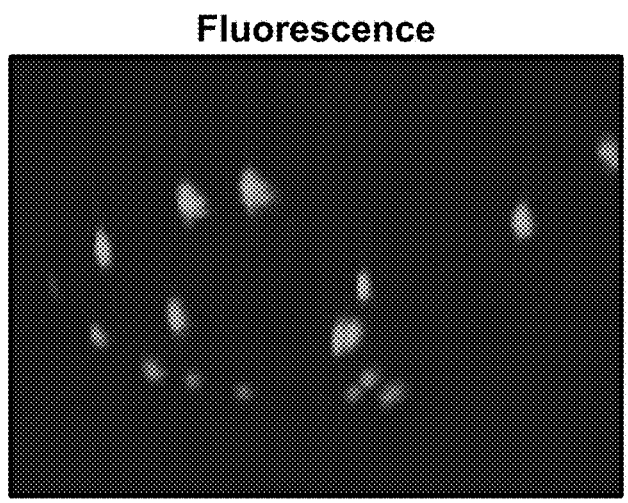
FIG. 20B shows a y-z cross section of the solution of FIG. 17 captured using fluorescence microscopy techniques, according to aspects of the present disclosure.
Figure 20C:
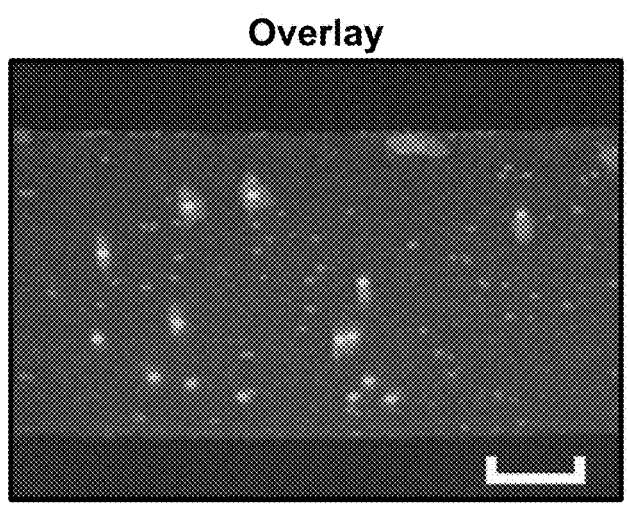
FIG. 20C shows the y-z cross sections of FIG. 20A and FIG. 20B overlaid on top of each other.

FIG. 18A shows an OCT cross-section in the x-y plane of the sample, while FIG. 18B shows an FM cross-section in the same x-y plane of the sample. As can be seen, the OCT cross section produces images of fluorescent and non-fluorescent microspheres, with the fluorescent microspheres appearing brighter in the OCT image. This is due to OCT's sensitivity to refractive index fluctuations in the sample. The OCT cross-section in FIG. 18A also shows the dust particle. The FM cross-section only shows the fluorescent microspheres. FIG. 18C shows an overlay of the two cross-sections of FIGS. 18A and 18B. As can be seen, the brighter microspheres in FIG. 18A correspond with the fluorescent microspheres in FIG. 18B. Thus, the overlaid cross-section in FIG. 18C shows the fluorescent microspheres from FIG. 18B appearing where the bright microspheres from FIG. 18A appeared. FIG. 18C also shows the non-fluorescent microspheres and the dust particle. FIGS. 19A-19C show an OCT cross-section, an FM cross-section, and an overlaid cross-section, respectively, in the x-z plane of the sample. FIGS. 20A-20C show an OCT cross-section, an FM cross-section, and an overlaid cross-section, respectively, in the y-z plane of the sample.

Figure 21:
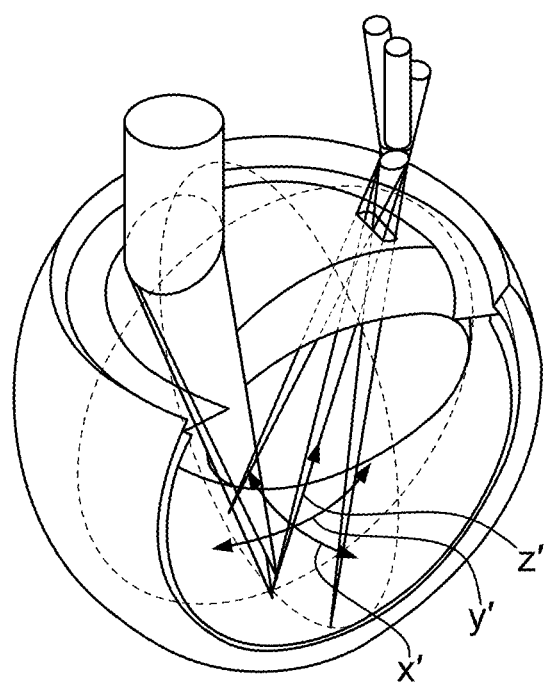
FIG. 21 shows the setup of a system for imaging an in vivo retina, according to aspects of the present disclosure.

Referring now to FIG. 21, an exemplary setup showing the imaging of an in vivo retina (i.e. an eye) is illustrated. Here, the lens used to create the oblique angle of incidence is not a separate optical component, but rather is the lens of the eye itself. As is shown in FIG. 21, the optical axis of the ocular lens is offset from the optical axis of the telescope system leading to the eye. This is illustrated by showing the incident electromagnetic radiation striking the lens away from the center of the lens. This offset thus causes the incident electromagnetic radiation to strike the retina itself at an oblique angle. The incident electromagnetic radiation follows the tilted z' axis. The emitted electromagnetic radiation is also shown being emitted from the retina and propagating through the lens.

Figure 22A:
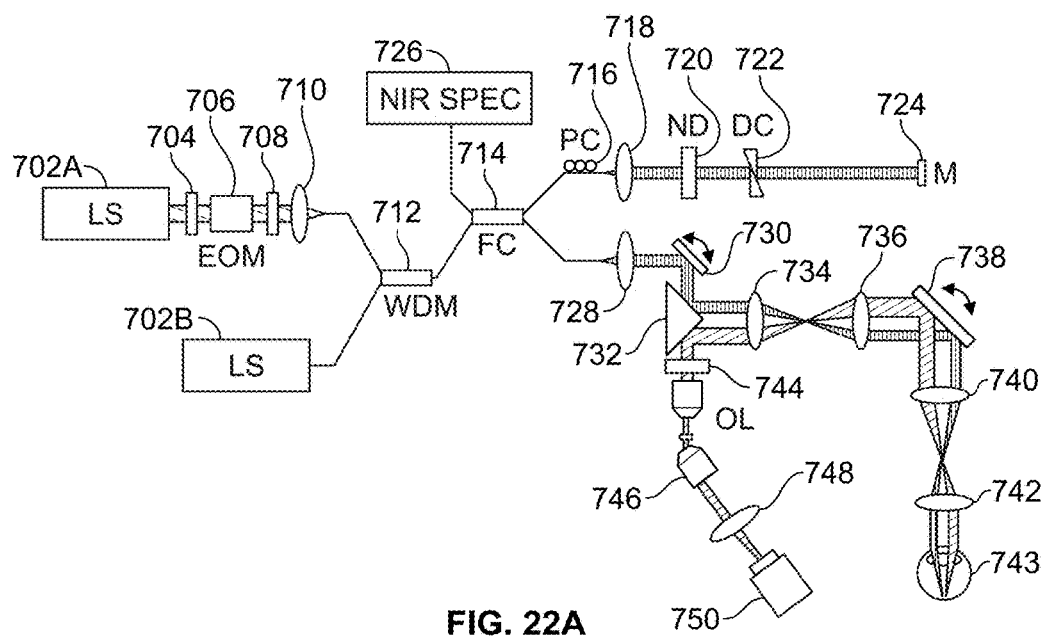
FIG. 22A shows an embodiment of a system for obtaining a three-dimensional image of a sample, according to aspects of the present disclosure.

Referring now to FIG. 22A, a system 700 for capturing a 3D image of an imaging target operates under similar principles as those described herein. Instead of the single light source that system 400 has, system 700 includes light source 702A and light source 702B. Light source 702A emits electromagnetic radiation that is used primarily for FM imaging, while light source 702B emits electromagnetic radiation that is used primarily for OCT imaging. Light source 702A can be, for example, a laser configured to emit electromagnetic radiation centered around a desired wavelength. In some implementations, the electromagnetic radiation emitted from light source 702A is between about 400 nm and about 500 nm, between about 450 nm and about 500 nm, between about 480 nm and about 490 nm, or between about 420 nm and about 470 nm. In other implementations, the electromagnetic radiation emitted from light source 702A is centered around 488 nm. In general, the light source 702A is selected such that the electromagnetic radiation emitted from the light source 702A is within the absorption wavelength range of the same to be imaged. Light source 702B can be, for example, a super luminescent diode that is configured to emit electromagnetic radiation in the reflection wavelength range of the sample, which can be between about 550 nm and about 700 nm, between about 800 nm and about 900 nm, or any other suitable wavelength range or value as needed to image the sample. Thus, light source 702A is configured to emit electromagnetic radiation in a first wavelength range, while light source 702B is configured to emit electromagnetic radiation in a second wavelength range.

Electromagnetic radiation emitted by light source 702A passes through a polarizer 704. Polarizer 704 is used to adjust the polarization state of electromagnetic radiation emitted from light source 702A so that it is properly polarized for use in FM imaging. The emitted electromagnetic radiation then passes through an electro-optic modulator 706, which can provide electrical control of the electromagnetic radiation being used for FM imaging. The electro-optic modulator 706 can also be used to implement scanned structure plane illumination of the sample. After emerging from the electro-optic modulator 706, the emitted electromagnetic radiation can pass through an analyzer 708 which can provide data and feedback to the person operating the system. The electromagnetic radiation emitted by light source 702A can then be focused by a lens 710 into one or more optical combination components. The electromagnetic radiation emitted by light source 702B is also input to the one or more optical combination components. In the implementation illustrated in FIG. 22A, the one or more optical combination components includes a wavelength division multiplexer 712 and an optical fiber coupler 714, which can be similar to optical fiber coupler 422 of FIG. 4. The wavelength division multiplexer 712 combines the electromagnetic radiation from light source 702A and 702B so that it can be directed to the sample.

The combined electromagnetic radiation is then output to a both a reference stage and a steering stage. The reference stage is generally similar to the reference stage of other implementations discussed herein, and is generally utilized in a similar fashion. The electromagnetic radiation in the reference stage (which is used as the reference arm for OCT imaging) passes through a polarization controller 716, which ensures that the polarization of the electromagnetic radiation propagating through the reference stage is identical to the polarization of the electromagnetic radiation propagating through the steering stage. The electromagnetic radiation in the reference stage is then collimated by a lens 718 and directed to a variable neutral density filter 720 to attenuate the power of the electromagnetic radiation propagating through the reference stage. This attenuation ensures that the OCT detection equipment is not oversaturated. The electromagnetic radiation then propagates through a dispersion compensator 722 to compensate for any dispersion introduced to the electromagnetic radiation propagating through the steering stage by the optical equipment in the steering stage. Finally, the electromagnetic radiation reflects off of a mirror 724 and propagates back through the reference stage until it reaches the optical fiber coupler 714. The electromagnetic radiation from the reference stage is then output to a first image capture device 726, which in some implementations can be a near infrared spectrometer (NIR SPEC), which is used for OCT detection.

In the steering stage, the combined electromagnetic radiation passes through a lens 728 and is focused onto a fast scanning mirror 730. The fast scanning mirror 730 is used to steer the electromagnetic radiation to a knife-edge prism mirror 732, which is in the shape of a right triangle, and thus is also known as a right angle prism mirror. As shown in FIG. 22A, the electromagnetic radiation in the steering stage is incident on a flat face of the knife-edge prism mirror 732 that is disposed at a 45° angle to thereby direct the combined electromagnetic radiation through a first telescope system containing lenses 734 and 736. The combined electromagnetic radiation is then incident on a slow scanning mirror 738, which steers the combined electromagnetic radiation into a second telescope system containing lenses 740 and 742. The combined electromagnetic radiation then propagates to the sample 743, which in FIG. 22A is shown as an eye. The optical axis of one or both of lenses 740 and 742 can be off-set from the optical axis of the first optical pathway such that the combined electromagnetic radiation is shifted by the lenses 740 and 742 and is incident on the sample 743 at an oblique angle, which can be in some implementations about 26 degrees.

Electromagnetic radiation incident on the sample 743 that is in the absorption wavelength range is absorbed by fluorescent structures in the sample, which in response emit electromagnetic radiation in the emission wavelength range. Incident electromagnetic radiation in the reflection wavelength range is reflected by structures in the sample 743. Together, the reflected electromagnetic radiation and the emitted electromagnetic radiation propagate back through lenses 742 and 740, slow scanning mirror 738, lenses 736 and 734, and fast-scanning mirror 734. Fast-scanning mirror 734 can steer the reflected electromagnetic radiation and the emitted electromagnetic radiation onto the knife-edge prism mirror 732. The reflected and emitted electromagnetic radiation is incident on a point of the knife-edge prism mirror 732 that corresponds to the interior right angle of the knife-edge prism mirror 732. By directing the electromagnetic radiation precisely onto the point of the knife-edge prism mirror 732, the electromagnetic radiation incident on the knife-edge prism mirror 732 is split into two separate beams of electromagnetic radiation 180° apart. The two telescope systems, the fast-scanning mirror 730, and the slow-scanning mirror 738 are thus able to precisely aim the incident electromagnetic radiation such that the knife-edge prism mirror 732 is able to separate the reflected electromagnetic radiation from the emitted electromagnetic radiation.

The emitted electromagnetic radiation (due to excitation of fluorescent structures in the sample) can be directed in a first direction, while the reflected electromagnetic radiation can be directed in a second direction. The emitted electromagnetic radiation passes through a filter 744 that is configured to filter out any reflected electromagnetic radiation that may have been incidentally directed in the first direction by the knife-edge prism mirror 732. The emitted electromagnetic radiation that passes through the filter 744 is directed to an angled imaging setup, which can include an objective lens 746, a lens 748, and an image capture device 750. These component scan be substantially similar to objective lens 474, lens 478, and image capture device 480 of FIG. 4. The emitted electromagnetic radiation is reflected back through the fast-scanning mirror 730 and lens 728, and then propagates through the fiber coupler 714 which directs the reflected electromagnetic radiation to the near-infrared spectrometer 726. The near-infrared spectrometer 726 and the image capture device 750 can then be used to construct images of the sample, as discussed herein.

As illustrated in FIG. 22A, the wavelength division multiplexer 712 and the optical fiber coupler 714 output the combined electromagnetic radiation onto a first optical pathway leading to the sample. The combined electromagnetic radiation propagates along the first optical pathway in a first direction until it is incident on the sample. The sample absorbs a first portion of the combined electromagnetic radiation corresponding to the electromagnetic radiation emitted by the first light source 702A and emits electromagnetic radiation in response. The sample reflects a second portion of the combined electromagnetic radiation corresponding to the electromagnetic radiation emitted by the second light source 702B. The reflected electromagnetic radiation and the emitted electromagnetic radiation travel back along the first optical pathway in a second direction back toward the sample, where they are incident upon an optical separation component, which can be, for example, the knife-edge prism mirror 732. The knife-edge prism mirror 732 is configured to direct the reflected electromagnetic radiation onto a second optical pathway and the reflected electromagnetic radiation onto a third optical pathway, leading to image capture devices 726 and 750, respectively.

Figure 22B:
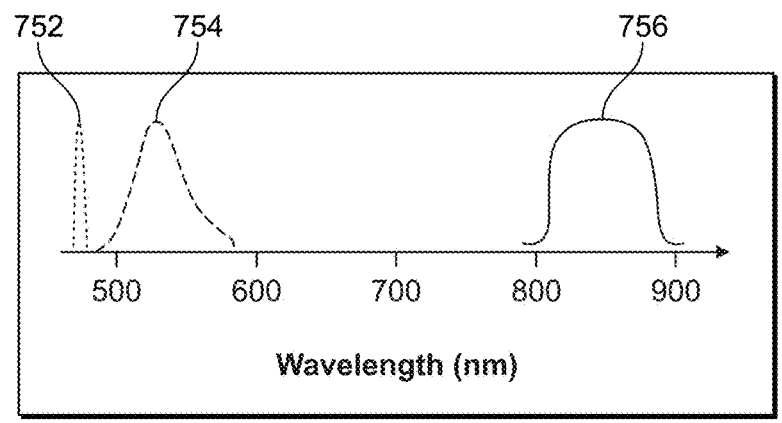
FIG. 22B shows an example fluorescence absorption spectrum of a sample, an example fluorescence emission spectrum of the sample, and an example optical coherence topography spectrum used with the sample; according to aspects of the present disclosure.

FIG. 22B illustrates the wavelength range of the various types of electromagnetic radiation that propagate through system 700 in one implementation. As shown, electromagnetic radiation 752, which is emitted by light source 702A, can centered around 488 nm, which generally corresponds to the absorption spectrum of the fluorescent structures in the sample 743. Electromagnetic radiation 754 is emitted by the fluorescent structures in the sample 743 and can be in a wavelength range of between about 490 nm, and about 590 nm, which generally corresponds to the emission spectrum of the fluorescent structures in the sample 743. Electromagnetic radiation 756 is emitted by light source 702B, and generally has a wavelength range of between about 800 nm and about 900 nm.

Alternative Implementations

Alternative Implementation 1. An optical system for producing a three-dimensional image of a sample, the optical system comprising: one or more electromagnetic radiation sources configured to produce electromagnetic radiation; a first optical pathway disposed between the one or more electromagnetic radiation sources and the sample, the produced electromagnetic radiation propagating in a first direction along an optical axis of the first optical pathway towards the sample; a lens disposed in the first optical pathway adjacent to the sample to focus the produced electromagnetic radiation onto the sample, an optical axis of the lens being offset from the optical axis of the first optical pathway such that the produced electromagnetic radiation is incident on the sample at an oblique angle, the sample reflecting a first portion of the incident electromagnetic radiation to produce reflected electromagnetic radiation, the sample absorbing a second portion of the incident electromagnetic radiation and responsive to the absorption of the second portion of the incident electromagnetic radiation, the sample emitting electromagnetic radiation; a second optical pathway disposed between the sample and a first image capture device, the reflected electromagnetic radiation propagating along the second optical pathway from the sample to the first image capture device, the reflected electromagnetic radiation being indicative of structural properties of the sample; and a third optical pathway disposed between the sample and a second image capture device, the emitted electromagnetic radiation propagating along the third optical pathway from the sample to the second image capture device, the emitted electromagnetic radiation being indicative of molecular properties of the sample.

Alternative Implementation 2. The optical system of Alternative Implementation 1, wherein the first portion of the incident electromagnetic radiation reflected by the sample includes electromagnetic radiation in a first wavelength range, and wherein the second portion of the incident electromagnetic radiation absorbed by the sample includes electromagnetic radiation in a second wavelength range.

Alternative Implementation 3. The optical system of Alternative Implementation 2, wherein the first wavelength range is different from the second wavelength range.

Alternative Implementation 4. The optical system of Alternative Implementation 1, further comprising an optical coupling component disposed in the first optical pathway to thereby form an initial stage and a steering stage.

Alternative Implementation 5. The optical system of Alternative Implementation 4, wherein the optical coupling component has a first port and a second port, the produced electromagnetic radiation propagating through the initial stage being incident on a first port of the optical coupling component and being output to the steering stage at the second port of the optical coupling component.

Alternative Implementation 6. The optical system of Alternative Implementation 5, wherein the produced electromagnetic radiation incident on the first port has a first intensity level, and wherein the electromagnetic radiation output at the second port has a second intensity level less than the first intensity level.

Alternative Implementation 7. The optical system of Alternative Implementation 4, wherein the initial stage includes one or more prisms to separate the produced electromagnetic radiation into discrete components based on wavelength, and a filter to remove the produced electromagnetic radiation having a wavelength equal to a wavelength of the emitted electromagnetic radiation.

Alternative Implementation 8. The optical system of Alternative Implementation 4, wherein the steering stage includes at least two scanning mirrors to steer the produced electromagnetic radiation.

Alternative Implementation 9. The optical system of Alternative Implementation 1, wherein the second optical pathway includes a first portion and a second portion, the first portion of second optical pathway having an optical axis that is coaxial with the optical axis of the first optical pathway such that the reflected electromagnetic radiation propagates along the first optical pathway in a second opposing direction away from the sample.

Alternative Implementation 10. The optical system of Alternative Implementation 9, wherein the second portion of the second optical pathway terminates at the first image capture device, and wherein an optical axis of the second portion of the second optical pathway is non-coaxial with the optical axis of the first optical pathway.

Alternative Implementation 11. The optical system of Alternative Implementation 1, further comprising an optical coupling component disposed in the first optical pathway to thereby form an initial stage, a steering stage, and a reference stage, the produced electromagnetic radiation propagating from the one or more electromagnetic radiation sources to a first port of the optical coupling component, the produced electromagnetic radiation being output at both a second port of the optical coupling component to the reference stage and a third port of the optical coupling component to the steering stage.

Alternative Implementation 12. The optical system of Alternative Implementation 11, wherein the second optical pathway has a first portion with an optical axis coaxial with an optical axis of the steering stage, and wherein the reflected electromagnetic radiation propagates through the first portion of the second optical pathway to the second port of the optical coupling component.

Alternative Implementation 13. The optical system of Alternative Implementation 12, wherein the reference stage includes a mirror, and wherein the produced electromagnetic radiation output at the third port of the optical coupling component propagates through the reference stage and is reflected by the mirror back to the third port of the optical coupling component.

Alternative Implementation 14. The optical system of Alternative Implementation 13, wherein both the reflected electromagnetic radiation from the first portion of the second optical pathway and the produced electromagnetic radiation from the reference stage are output at a fourth port of the optical coupling component to the second portion of the second optical pathway.

Alternative Implementation 15. The optical system of Alternative Implementation 14, wherein the electromagnetic radiation output at the fourth port of the optical coupling component propagates through the second portion of the second optical pathway to the first image capture device.

Alternative Implementation 16. The optical system of Alternative Implementation 1, wherein the optical axis of the lens is offset from the optical axis of the first optical pathway by about 4 millimeters, and wherein the oblique angle is about 26 degrees.

Alternative Implementation 17. The optical system of Alternative Implementation 1, wherein the sample is a retina of an eye, and wherein the lens disposed in the first optical pathway is a lens of the eye.

Alternative Implementation 18. The optical system of Alternative Implementation 17, wherein the retina is an in vivo retina of a person.

Alternative Implementation 19. A method of obtaining a three-dimensional image of a sample, the method comprising: producing electromagnetic radiation from one or more electromagnetic radiation sources; directing the produced electromagnetic radiation such that the produced electromagnetic radiation propagates through a lens and is incident on the sample at an oblique angle, the sample reflecting a first portion of the incident electromagnetic radiation to produce reflected electromagnetic radiation, the sample absorbing a second portion of the incident electromagnetic radiation and responsive to the absorption of the second portion of the incident electromagnetic radiation, the sample emitting electromagnetic radiation; scanning the incident electromagnetic radiation across a surface area of the sample; recording the reflected electromagnetic radiation while scanning the incident electromagnetic radiation across the surface of the sample to produce a first plurality of cross-sectional images of the sample; recording the emitted electromagnetic radiation while scanning the incident electromagnetic radiation across the surface of the sample to produce a second plurality of cross-sectional images of the sample; modifying the first and second plurality of cross-sectional images to compensate for the oblique angle of the incident electromagnetic radiation; and producing a three-dimensional image from the first plurality of modified cross-sectional images and the second plurality of modified cross-sectional images.

Alternative Implementation 20. The method of Alternative Implementation 19, wherein the scanning step further comprises: scanning the incident electromagnetic radiation across a surface of the sample in a first direction, the incident electromagnetic radiation being scanned in discrete increments to a plurality of discrete locations on the surface of the sample; for each discrete location on the surface of the sample, scanning the incident electromagnetic radiation across the surface of the sample in a second direction orthogonal to the first direction.

Alternative Implementation 21. The method of Alternative Implementation 19, wherein the producing step further comprises: combining each of the first plurality of modified cross-sectional images to create a first three-dimensional image of the sample; combining each of the second plurality of modified cross-sectional images to create a second three-dimensional image of the sample; and co-registering the first three-dimensional image of the sample and the second three-dimensional image of the sample to create a third three-dimensional image of the sample.

Alternative Implementation 22. The method of Alternative Implementation 19, wherein the sample is a retina of an eye, and wherein the lens is a lens of the eye.

Alternative Implementation 23. The method of Alternative Implementation 22, wherein the retina is an in vivo retina of a person.

Alternative Implementation 24. The method of Alternative Implementation 22, wherein the second portion of the incident electromagnetic radiation is absorbed by fluorophores in the retina.

Alternative Implementation 25. The method of Alternative Implementation 24, wherein the fluorophores in the retina are artificial fluorophores that are placed in the retina prior to imaging.

Alternative Implementation 26. The method of Alternative Implementation 24, wherein the fluorophores in the retina are naturally-occurring fluorophores.

Alternative Implementation 27. An optical system for producing a three-dimensional image of a sample, the optical system comprising: a first electromagnetic radiation source configured to produce electromagnetic radiation in a first wavelength range; a second electromagnetic radiation source configured to produce electromagnetic radiation in a second wavelength range; one or more optical combination components configured to combine the electromagnetic radiation in the first wavelength range and the electromagnetic radiation in the second wavelength range, the combined electromagnetic radiation including a first portion of electromagnetic radiation in the first wavelength range and a second portion of electromagnetic radiation in the second wavelength range; a first optical pathway disposed between the one or more optical combination components and the sample, the combined electromagnetic radiation from the one or more optical combination components configured to propagate along the first optical pathway in a first direction such that it is incident on the sample, the sample reflecting the first portion of the combined electromagnetic radiation to produce reflected electromagnetic radiation, the sample absorbing the second portion of the combined electromagnetic radiation and responsive to the absorption of the second portion of the combined electromagnetic radiation, the sample emitting electromagnetic radiation, the reflected electromagnetic radiation and the emitted electromagnetic radiation propagating along the first optical pathway in a second direction; and an optical separation component disposed in the first optical pathway, the optical separation component directing the reflected electromagnetic radiation along a second optical pathway to a first image capture device and directing the emitted electromagnetic radiation along a third optical pathway to a second image capture device, the reflected electromagnetic radiation being indicative of structural properties of the sample, the emitted electromagnetic radiation being indicative of molecular properties of the sample.

Alternative Implementation 28. The optical system of Alternative Implementation 27, wherein the optical separation component includes a knife-edge prism mirror.

Alternative Implementation 29. The optical system of Alternative Implementation 28, wherein the knife-edge prism mirror has a triangular shape with an interior right angle, and wherein both the reflected electromagnetic radiation and the emitted electromagnetic radiation are generally incident upon an exterior point of the triangular shape corresponding to the interior right angle.

Alternative Implementation 30. The optical system of Alternative Implementation 27, wherein the first electromagnetic radiation source is a laser configured to emit electromagnetic radiation in the first wavelength range, and wherein the second electromagnetic radiation source is a super luminescent diode configured to emit electromagnetic radiation in the second wavelength range.

Alternative Implementation 31. The optical system of Alternative Implementation 27, wherein the first wavelength range is different than the second wavelength range.

Alternative Implementation 32. The optical system of Alternative Implementation 27, further comprising one or more lenses disposed in the first optical pathway, the one or more lenses configured to direct the combined electromagnetic radiation onto the sample.

Alternative Implementation 33. The optical system of Alternative Implementation 32, wherein an optical axis of at least one of the one or more lenses is offset from an optical axis of the first pathway such that the combined electromagnetic radiation is incident on the sample at an oblique angle.

Alternative Implementation 34. The optical system of Alternative Implementation 33, wherein the oblique angle is about 26 degrees.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

What is claimed is:

1. An optical system for producing a three-dimensional image of a sample, the optical system comprising:
    one or more electromagnetic radiation sources configured to produce electromagnetic radiation;
    a first optical pathway disposed between the one or more electromagnetic radiation sources and the sample, the produced electromagnetic radiation propagating in a first direction along an optical axis of the first optical pathway towards the sample;
    a lens disposed in the first optical pathway adjacent to the sample to focus the produced electromagnetic radiation onto the sample, an optical axis of the lens being offset from the optical axis of the first optical pathway such that the produced electromagnetic radiation is incident on the sample at an oblique angle, the sample reflecting a first portion of the incident electromagnetic radiation to produce reflected electromagnetic radiation, the sample absorbing a second portion of the incident electromagnetic radiation and responsive to the absorption of the second portion of the incident electromagnetic radiation, the sample emitting electromagnetic radiation;
    a second optical pathway disposed between the sample and a first image capture device, the reflected electromagnetic radiation propagating along the second optical pathway from the sample to the first image capture device, the reflected electromagnetic radiation being indicative of structural properties of the sample; and
    a third optical pathway disposed between the sample and a second image capture device, the emitted electromagnetic radiation propagating along the third optical pathway from the sample to the second image capture device, the emitted electromagnetic radiation being indicative of molecular properties of the sample.

2. The optical system of claim 1, wherein the first portion of the incident electromagnetic radiation reflected by the sample includes electromagnetic radiation in a first wavelength range, and wherein the second portion of the incident electromagnetic radiation absorbed by the sample includes electromagnetic radiation in a second wavelength range.

3. The optical system of claim 2, wherein the first wavelength range is different from the second wavelength range.

4. The optical system of claim 1, further comprising an optical coupling component disposed in the first optical pathway to thereby form an initial stage and a steering stage.

5. The optical system of claim 4, wherein the initial stage includes one or more prisms to separate the produced electromagnetic radiation into discrete components based on wavelength, and a filter to remove the produced electromagnetic radiation having a wavelength equal to a wavelength of the emitted electromagnetic radiation.

6. The optical system of claim 1, wherein the second optical pathway includes a first portion and a second portion, the first portion of second optical pathway having an optical axis that is coaxial with the optical axis of the first optical pathway such that the reflected electromagnetic radiation propagates along the first optical pathway in a second opposing direction away from the sample.

7. The optical system of claim 6, wherein the second portion of the second optical pathway terminates at the first image capture device, and wherein an optical axis of the second portion of the second optical pathway is non-coaxial with the optical axis of the first optical pathway.

8. The optical system of claim 1, further comprising an optical coupling component disposed in the first optical pathway to thereby form an initial stage, a steering stage, and a reference stage, the produced electromagnetic radiation propagating from the one or more electromagnetic radiation sources to a first port of the optical coupling component, the produced electromagnetic radiation being output at both a second port of the optical coupling component to the reference stage and a third port of the optical coupling component to the steering stage.

9. The optical system of claim 8, wherein the second optical pathway has a first portion with an optical axis coaxial with an optical axis of the steering stage, and wherein the reflected electromagnetic radiation propagates through the first portion of the second optical pathway to the second port of the optical coupling component.

10. The optical system of claim 9, wherein the reference stage includes a mirror, and wherein the produced electromagnetic radiation output at the third port of the optical coupling component propagates through the reference stage and is reflected by the mirror back to the third port of the optical coupling component.

11. The optical system of claim 1, wherein the optical axis of the lens is offset from the optical axis of the first optical pathway by about 4 millimeters, and wherein the oblique angle is about 26 degrees.

12. The optical system of claim 1, wherein the sample is a retina of an eye, and wherein the lens disposed in the first optical pathway is a lens of the eye.

13. A method of obtaining a three-dimensional image of a sample, the method comprising:
    producing electromagnetic radiation from one or more electromagnetic radiation sources;
    directing the produced electromagnetic radiation such that the produced electromagnetic radiation propagates through a lens and is incident on the sample at an oblique angle, the sample reflecting a first portion of the incident electromagnetic radiation to produce reflected electromagnetic radiation, the sample absorbing a second portion of the incident electromagnetic radiation and responsive to the absorption of the second portion of the incident electromagnetic radiation, the sample emitting electromagnetic radiation;
    scanning the incident electromagnetic radiation across a surface area of the sample;
    recording the reflected electromagnetic radiation while scanning the incident electromagnetic radiation across the surface of the sample to produce a first plurality of cross-sectional images of the sample;
    recording the emitted electromagnetic radiation while scanning the incident electromagnetic radiation across the surface of the sample to produce a second plurality of cross-sectional images of the sample;
    modifying the first and second plurality of cross-sectional images to compensate for the oblique angle of the incident electromagnetic radiation; and
    producing a three-dimensional image from the first plurality of modified cross-sectional images and the second plurality of modified cross-sectional images.

14. The method of claim 13, wherein the scanning step further comprises:
    scanning the incident electromagnetic radiation across a surface of the sample in a first direction, the incident electromagnetic radiation being scanned in discrete increments to a plurality of discrete locations on the surface of the sample;
    for each discrete location on the surface of the sample, scanning the incident electromagnetic radiation across the surface of the sample in a second direction orthogonal to the first direction.

15. The method of claim 13, wherein the producing step further comprises:
    combining each of the first plurality of modified cross-sectional images to create a first three-dimensional image of the sample;
    combining each of the second plurality of modified cross-sectional images to create a second three-dimensional image of the sample; and
    co-registering the first three-dimensional image of the sample and the second three-dimensional image of the sample to create a third three-dimensional image of the sample.

16. The method of claim 13, wherein the sample is a retina of an eye, and wherein the lens is a lens of the eye.

17. The method of claim 16, wherein the second portion of the incident electromagnetic radiation is absorbed by fluorophores in the retina.

18. An optical system for producing a three-dimensional image of a sample, the optical system comprising:
    a first electromagnetic radiation source configured to produce electromagnetic radiation in a first wavelength range;
    a second electromagnetic radiation source configured to produce electromagnetic radiation in a second wavelength range;
    one or more optical combination components configured to combine the electromagnetic radiation in the first wavelength range and the electromagnetic radiation in the second wavelength range, the combined electromagnetic radiation including a first portion of electromagnetic radiation in the first wavelength range and a second portion of electromagnetic radiation in the second wavelength range;
    a first optical pathway disposed between the one or more optical combination components and the sample, the combined electromagnetic radiation from the one or more optical combination components configured to propagate along the first optical pathway in a first direction such that it is incident on the sample, the sample reflecting the first portion of the combined electromagnetic radiation to produce reflected electromagnetic radiation, the sample absorbing the second portion of the combined electromagnetic radiation and responsive to the absorption of the second portion of the combined electromagnetic radiation, the sample emitting electromagnetic radiation, the reflected electromagnetic radiation and the emitted electromagnetic radiation propagating along the first optical pathway in a second direction; and
    an optical separation component disposed in the first optical pathway, the optical separation component directing the reflected electromagnetic radiation along a second optical pathway to a first image capture device and directing the emitted electromagnetic radiation along a third optical pathway to a second image capture device, the reflected electromagnetic radiation being indicative of structural properties of the sample, the emitted electromagnetic radiation being indicative of molecular properties of the sample.

19. The optical system of claim 18, wherein the optical separation component includes a knife-edge prism mirror.

20. The optical system of claim 19, wherein the knife-edge prism mirror has a triangular shape with an interior right angle, and wherein both the reflected electromagnetic radiation and the emitted electromagnetic radiation are generally incident upon an exterior point of the triangular shape corresponding to the interior right angle.

* * * * *